United States Patent [19]

Yabusaki et al.

[11] Patent Number: 5,114,852
[45] Date of Patent: May 19, 1992

[54] CHIMERIC FUSED MONOOXYGENASE OF CYTOCHROME P-450 AND NADPH-CYTOCHROME P-450 REDUCTASE

[75] Inventors: Yoshiyasu Yabusaki; Hiroko Murakami, both of Hyogo; Toshiyuki Sakai; Megumi Shibata, both of Osaka; Hideo Ohkawa, Hyogo, all of Japan

[73] Assignee: Director-General of Agency of Industrial Science & Technology, Tokyo, Japan

[21] Appl. No.: 500,220

[22] Filed: Mar. 27, 1990

Related U.S. Application Data

[63] Continuation of Ser. No. 81,647, Aug. 4, 1987, abandoned.

[30] Foreign Application Priority Data

Aug. 12, 1986 [JP] Japan .................... 61-187713

[51] Int. Cl.[5] .................... C12N 9/02; C07K 13/00
[52] U.S. Cl. .................... 435/189; 430/401; 435/27; 435/47
[58] Field of Search .................... 435/189, 172.3, 47, 435/27; 530/401

[56] References Cited

U.S. PATENT DOCUMENTS 4,766,068  8/1988  Oeda et al. .................... 435/68
4,774,180  9/1988  Toth et al. .................... 435/68

OTHER PUBLICATIONS

Genetically Engineered Modification of P450 Monooxygenases: ... Enzyme, Yabushiki et al., DNA, vol. 7, No. 10, 1988, pp. 701-711.
Oeda, K., et al., (1985), DNA 4(3), 203-210.
Murakami, H., et al., (1986), DNA 5(1), 1-10.
Yabusaki, Y., et al., (1984), J. Biochem., 96, 793-804.
Yabusaki, Y., et al., (1984), Nucl. Acids Res., 12(6), 2929-2938.
Narhi, L. O., et al., (1986), J. Biol. Chem., 261(16), 7160-7169.

*Primary Examiner*—Charles L. Patternson
*Attorney, Agent, or Firm*—Ladas & Parry

[57] ABSTRACT

The present invention provides a chimeric enzyme gene which codes for a monooxygenase having both monooxygenase activity derived from cytochrome P-450 and reducing power supplying ability derived from NADPH-cytochrome P-450 reductase.

The present invention further provides a yeast expression plasmid which contains said chimeric enzyme gene and expresses said monooxygenase gene; a transformed yeast strain which carries said yeast expression plasmid; a monooxygenase which has both the monooxygenase activity and the reducing power supplying ability as mentioned above; and a process for producing said monooxygenase.

9 Claims, 40 Drawing Sheets

FIG. 2 (1)

```
       10              20              30              40              50              60              70              80
ATGCCTTCTGTGTATGGATTCCCAGCCTTCACATCAGCCACAGAGCTGCTCCTGGCCGTCACCACATTCTGCCTT
MetProSerValTyrGlyPheProAlaPheThrSerAlaThrGluLeuLeuLeuLeuAlaValThrThrPheCysLeu 85              95             105             115             125             135             145             155
GGATTCTGGGTGGTTAGAGTCACAAGAGTCTGGGTTCCCAAAGGTCTGAAGAGTCCACCCGGAGACCTGGGGCTTG
GlyPheTrpValValArgValThrArgValProLysGlyLeuLysSerProProGlyProTrpGlyLeu 160             170             180             190             200             210             220             230
CCCTTCATAGGGCACGTGCTGCTCAAACCTGGGGAAGAACCCACACCTGTCACTGACAAAACTGAGTCAGCAGTATGGG
ProPheIleGlyHisValLeuThrLeuGlyLysLysAsnProHisLeuSerLeuThrLysLeuSerGlnGlnTyrGly 235             245             255             265             275             285             295             305
GACGTGCTGCAGATCCGTATTGGCTCCACACCCCTGGTGGTTGTGGTAGTCAGCGGCCTG
AspValLeuGlnIleArgIleGlySerThrProValValLeuSerGlyLeuAsnThrIleLysGlnAlaLeu 310             320             330             340             350             360             370             380
GACTTCAAAGGCCTGGATGACTTCAAAGGCGGCCGGCCTCAAAGCCCGGGGATGACTTCAAAGGCGGCCGGCCTCAAAGCCCAGACTTCACACTTATGGCTAATGGCCAGAGCATG
ValLysGlnGlyAspAspPheLysGlyArgProAspLeuTyrSerPheThrLeuIleAlaAsnGlyGlnSerMet 385             395             405             415             425             435             445             455
ACTTTCAACCCAGACTCTGGCCCTCTGTGGCTGGCCCCCAGAATGCGCTGAAGAGTTTCTCC
ThrPheAsnProAspSerGlyProLeuTrpAlaAlaArgArgLeuAlaGlnAsnAlaLeuLysSerPheSer 460             470             480             490             500             510             520             530
ATAGCCTCAGACCCCAACACTGGCATCCCTCTGCTACTTGGAAGAGGCAAAGAGGCTGAGCACGTGAGCAAAGAGGCTGAATACTTAATC
IleAlaSerAspProThrLeuAlaSerSerCysTyrLeuGluHisValSerLysGluAlaGluTyrLeuIle
```

FIG. 2(2)

```
       535         545         555         565         575         585         595         605
AGCAAGTTCCAGAAGCTGATGGCAGAGGTTGGCCACTTGGCCACCCTTCGACCCTTCAAGTATTTGGTGGTCAGTGGCCAAT
SerLysPheGlnLysLeuMetAlaGluValGlyHisPheAspProPheLysLysTyrLeuValValSerValAlaAsn 610         620         630         640         650         660         670         680
GTCATCTGCTGCCATATGCTTGGGCAGAGACGTTATGACCACGATGACCAAGAGCTGCTCAGCATAGTCAATCTAAGC
ValIleCysAlaIleCysPheGlyArgArgTyrAspHisAspAspGlnGluLeuLeuSerIleValAsnLeuSer 685         695         705         715         725         735         745         755
AATGAGTTTGGGGAGGTTACTGGTTCTGGATACCCAGCTGACTTCATTCCTATCCTCCGTTACCTCCCTAACTCT
AsnGluPheGlyGluValThrGlySerGlyTyrProAlaAspPheIleProIleLeuArgTyrLeuProAsnSer 760         770         780         790         800         810         820         830
TCCCTGGATGCCTTCAAGGACTTGAATAAGAAGTTCTACAGTTTCATGAAGAAGCTAATCAAAGAGCACTACAGG
SerLeuAspAlaPheLysAspLeuAsnLysLysPheTyrSerPheMetLysLysLeuIleLysGluHisTyrArg 835         845         855         865         875         885         895         905
ACATTTGAGAAGGGCCACATCCGGGACATTGTCAGGACCTTCATTGAGCATTGTCAGGACAGGAGGCTGGACGAG
ThrPheGluLysGlyHisIleArgAspIleThrAspIleThrAspSerArgLeuIleGluHisCysGlnAspArgArgLeuAspGlu 910         920         930         940         950         960         970         980
AATGCCAATGTCCAGCTCTCAGATGATAAGGTCATTACGATTGTTTTGAAGCTTTTTGACCTCTTTGGAGCTGGGTTTGACACA
AsnAlaAsnValGlnLeuSerAspAspLysValIleThrIleValPheAspLeuPheGlyAlaGlyPheAspThr 985         995         1005        1015        1025        1035        1045        1055
ATCACAACTGCTATCTCTTGGAGCCTCATGTACCTGGTAACCAACCCTAGGATACAGAGAAAGATCCAGGAGGAG
IleThrThrAlaIleSerTrpSerLeuMetTyrLeuValThrAsnProArgIleGlnArgLysIleGlnGluGlu
```

FIG. 2(3)

```
                1060      1070      1080      1090      1100      1110      1120      1130
           TTAGACACAGTGATGGCAGGGATCGGCAGCCCCCGGCTTTCTGACAGACCTCAGCTGCCTGCCTATCTGGAGCCCTTC
           LeuAspThrValIleGlyArgAspArgGlnProArgLeuSerAspArgProGlnLeuProTyrLeuGluAlaPhe
                1135      1145      1155      1165      1175      1185      1195      1205
           ATCCTGGAGACCTTCCGACATTCATCCTTTGTCCCCACAGCACCACCATAAGAGATACAAGTCTG
           IleLeuGluThrPheArgHisSerPheValProPheThrIleProHisSerThrIleArgAspThrSerLeu
                1210      1220      1230      1240      1250      1260      1270      1280
           AATGGCTTCTATATCCCCAAGGGACACTGTGTCTTTGTGAACCAGTGGCAGGTTAACCATGACCAGGAACTATGG
           AsnGlyPheTyrIleProLysGlyHisCysValPheValAsnGlnTrpGlnValAsnHisAspGlnGluLeuTrp
                1285      1295      1305      1315      1325      1335      1345      1355
           GGTGATCCAAACGAGTTCCCGGCCTGAAAGGTTTCTTACCTCCAGTGGCACTCTGGACAAAACACCTGAGTGAGAAG
           GlyAspProAsnGluPheArgProGluArgPheLeuThrSerSerGlyThrLeuAspLysHisLeuSerGluLys
                1360      1370      1380      1390      1400      1410      1420      1430
           GTCATTCTCTTCTTTGGTTGGGCAAGCGAAAGTGCATTGGGGGAGACCATTGGCCGACTGGAGGTCTTTTCTCCTG
           ValIleLeuPheGlyLeuGlyLysArgLysCysIleGlyGluThrIleGlyArgLeuGluValPheLeuPheLeu
                1435      1445      1455      1465      1475      1485      1495      1505
           GCCATCTTGCTGCAGCAAATGGAATTTAATGTCTCACCAGGCGAGAAGGTGGATATGACTCCTGCCTATGGGCTG
           AlaIleLeuLeuGlnGlnMetGluPheAsnValSerProGlyGluLysValAspMetThrProAlaTyrGlyLeu
                1510      1520      1530      1540      1550      1560      1570      1580
           ACTTTAAAACATGCCCGCTGTGAGCACTTCCAAGTGCAGATGCGGTCCTTCTGGTCCTCGAGCCATGATCCAAACA
           ThrLeuLysHisAlaArgCysGluHisPheGlnValGlnMetArgSerSerGlyProArgAlaMetIleGlnThr
```

FIG. 2(4)

```
     1585       1595       1605       1615       1625       1635       1645      1655
ACGGCCCACCCCTCAAAGAGAGCAGCTTCCTGGAAAAGATGAAGAAAACGGGAAGAACATTATCGTATTCTAT
ThrAlaProProValLysGluSerSerPheValGluLysMetLysLysThrGlyArgAsnIleIleValPheTyr 1660       1670       1680       1690       1700       1710       1720      1730
GGCTCCCAGACGGGAACCGCTGAGGAGTTTGCCAACCGGCTGTCCAAGGATGCCCACCGCTACGGGATGCGGGGC
GlySerGlnThrGlyThrAlaGluGluPheAlaAsnArgLeuSerLysAspAlaHisArgTyrGlyMetArgGly 1735       1745       1755       1765       1775       1785       1795      1805
ATGTCCGCAGACCCTGAAGAGTATGACTTGGCCGACCTGAGCAGCCTGGAGATCGACAAGTCCCTGGTAGTC
MetSerAlaAspProGluGluTyrAspLeuAlaAspLeuSerSerLeuProGluIleAspLysSerLeuValVal 1810       1820       1830       1840       1850       1860       1870      1880
TTCTGCATGGCCACATACGGAGAGGGCGACCCCACGGACAATGCCCAGGACTTCTATGACTGGCTCCAGGAGACT
PheCysMetAlaThrTyrGlyGluGlyAspProThrAspAsnAlaGlnAspPheTyrAspTrpLeuGlnGluThr 1885       1895       1905       1915       1925       1935       1945      1955
GACGTGGACCTCACTGGGTCAAGTTGCTGTATTGGTCTTGGGAACAAGACCTATGAGCACTTCAATGCCATG
AspValAspLeuThrGlyValLysPheAlaValPheGlyLeuGlyAsnLysThrTyrGluHisPheAsnAlaMet 1960       1970       1980       1990       2000       2010       2020      2030
GGCAAGTATGTGGACCAGCTGGAGCAGCTTGGCGCCCAGGCATCTTTGAGTTGGCCCTTGCTGGGCTTGGATGATGAC
GlyLysTyrValAspGlnLeuGluGlnLeuGlyAlaGlnArgIlePheGluLeuGlyLeuGlyAspAspAsp 2035       2045       2055       2065       2075       2085       2095      2105
GGGAACTTGGAAGAGGATTTCATCACGTGGAGGGAGCAGTTCTGCCAGTTCTTTGGGGTAGAA
GlyAsnLeuGluGluAspPheIleThrTrpArgGluGlnPheProAlaValCysGluPhePheGlyValGlu
```

FIG. 2 (5)

```
         2110      2120      2130      2140      2150      2160      2170     2180
GCCACTGGGGAGGAGTCGAGCATTCGCCAGTATGAGCTCGTTGGTCCACGAAGACATGGACGTAGCCAAGGTGTAC
AlaThrGlyGluGluSerSerIleArgGlnTyrGluLeuValHisGluAspMetAspValAlaLysValTyr 2185      2195      2205      2215      2225      2235      2245      2255
ACGGGTGAGATGGGCCGTCTGAAGAGCTACGAGCTTGAAGAGCTACAAGGACTACGAGAACCAGAGAACTGCTAAGAATCCATTCCTGGCT
ThrGlyGluMetGlyArgLeuLysSerTyrGluAsnGlnLysProProPheAspAlaLysAsnProPheLeuAla 2260      2270      2280      2290      2300      2310      2320      2330
GCTGTGACCGCCAACCGGAAGCTGAACCGGAAGCTGAACCAAGGCACTGAGCGGCATCTAATGCACCTGGAGTTGGACATCTCAGAC
AlaValThrAlaAsnArgLysLeuAsnGlnGlyThrGluArgHisLeuMetHisLeuGluLeuAspIleSerAsp 2335      2345      2355      2365      2375      2385      2395      2405
TCCAAGATCAGGTATGAATCTGGAGATCACGTGAGTCATCACGTGGCTGTGTACCCAGCCAATGACTCAGCCCTGGTCAACCAGATT
SerLysIleArgTyrGluSerGlyAspHisValAlaValTyrProAlaAsnAspSerAlaLeuValAsnGlnIle 2410      2420      2430      2440      2450      2460      2470      2480
GGGGAGATCCTCGGGAGCTGACCTGGATGTCATCATGTCTCTAAACAATCTCGATGAGGAGTCAAACAAGAAGCAT
GlyGluIleLeuGlyAlaAspLeuValIleMetSerLeuAsnAsnLeuAspGluGluSerAsnLysLysHis 2485      2495      2505      2515      2525      2535      2545      2555
CCGTTCCCCTGCCCCACCACCTACCGGACGGCCCCTCACCTGGACATCACTGGACATCACTAACCCGCCACGCACCAAT
ProPheProCysProThrThrTyrArgThrAlaLeuThrTyrLeuAspIleThrAsnProProArgThrAsn 2560      2570      2580      2590      2600      2610      2620      2630
GTGCTCTACGAACTGGCACAGTACGGCCTCGAGAGCCCCTCGGAGCAGGAGCACCTGCACAAGATGGCGTCATCCTCA
ValLeuTyrGluLeuAlaGlnTyrAlaSerGluProSerGluGlnGluHisLeuHisLysMetAlaSerSer
```

FIG. 2(6)

```
      2635      2645      2655      2665      2675      2685      2695      2705
GGCGAGGGCAAGGAGAGCTGTACCTGAGCTGGGTGGTGGTGGAAGCCCGGAGGCACACTCTAGCCATCCTCCAAGACTAC
GlyGluGlyLysGluLeuTyrLeuSerTrpLeuValValGluAlaArgHisIleLeuAlaIleLeuGlnAspTyr 2710      2720      2730      2740      2750      2760      2770      2780
CCATCACTGCGGCCACCATCGACCACCACCACCACCACCTGTGTGAGCTGTGCTGCTGCAGGCCCTGCCAGGCCCGATACTACCTTCCATTGCC
ProSerLeuArgProProIleAspHisLeuCysGluLeuLeuProArgLeuGlnAlaArgTyrTyrSerIleAla 2785      2795      2805      2815      2825      2835      2845      2855
TCATCCTCCAAGTCCACCCCAACTCCGTGCACATCTGTCCTGCCCTGGAGTACGAAGCCAAGTCTGCCCGA
SerSerSerLysValHisProAsnSerValHisIleCysAlaAlaValGluTyrGluAlaLysSerGlyArg 2860      2870      2880      2890      2900      2910      2920      2930
GTGAACAAGGGGTGGCCACTAGCTGGCTTCGGGCCAAGGAACCAGCAGGCGAGAATGGGCCCGCCCTGGTA
ValAsnLysGlyValAlaThrSerTrpLeuArgAlaLysGluProAlaGlyGluAsnGlyGlyArgAlaLeuVal 2935      2945      2955      2965      2975      2985      2995      3005
CCCATGTTCGTGCGCAAATCTCAGTTCCGCTTGCCTTCAAGTCCACCACACCTGTCATCATGGTGGGCCCCGGC
ProMetPheValArgLysSerGlnPheArgLeuProPheLysSerThrThrProValIleMetValGlyProGly 3010      3020      3030      3040      3050      3060      3070      3080
ACTGGGATTGCCCCCTTTCATGGGCTTCATCCAGGAACGAGCTTGGCTTCGAGAGCAAGGAGCAAGGAGGTGGGAGAG
ThrGlyIleAlaProPheMetGlyPheIleGlnGluArgAlaTrpLeuArgGluGlyLysGluValGlyGluGlu 3085      3095      3105      3115      3125      3135      3145      3155
ACGCTGCTATACTATGGCTGCCGGGACTCGGATGAGGACTATCTGTACCGTGAAGAGCTAGCCCGCTTCCACAAG
ThrLeuLeuTyrTyrGlyCysArgArgSerArgAspGluAspTyrLeuTyrArgGluGluLeuAlaArgPheHisLys
```

FIG. 2 (7)

```
       3160       3170       3180       3190       3200       3210       3220       3230
GACGGTGCCCTCACGCAGCTTAATGTGGCCTTTCCCGGGAGCAGGCCCACAAGGTCTATGTCCAGCACCTTCTG
AspGlyAlaLeuThrGlnLeuAsnValAlaPheSerArgGluGlnAlaHisLysValTyrValGlnHisLeuLeu 3235       3245       3255       3265       3275       3285       3295       3305
AAGAGAGACAGGGAACACCTGTGGAAGCTGATCCAAGGGCGGTGCCCACATCTATGTGTGCGGGGATGCTCGA
LysArgAspArgGluHisLeuTrpLysLeuIleHisGlyAlaHisIleTyrValCysGlyAspAlaArg 3310       3320       3330       3340       3350       3360       3370       3380
AATATGGCCAAAGATGTGCAAAACACATTCTATGACATTGTGGCTGAGTTCGGGCCCATGGAGCACACCCAGGCT
AsnMetAlaLysAspValGlnAsnThrPheTyrAspIleValAlaGluPheGlyProMetGluHisThrGlnAla 3385       3395       3405       3415       3425       3435
GTGGACTATGTTAAGAAGCTGATGACCAAGGGCCGCTACTCACTAGATGTGTGGAGCTAG
ValAspTyrValLysLysLeuMetThrLysGlyArgTyrSerLeuAspValTrpSer***
```

FIG. 3 (1)

```
         10         20         30         40         50         60         70         80
ATGCCCTTCTGTGTATGGATTCCCAGCCTTCACATCAGCCACAGAGCTGCTTCCTCTGGCCGTCCTGCCCTTCACCACATTCTGCCTT
MetProSerValTyrGlyPheProAlaPheThrSerAlaThrGluLeuLeuLeuAlaValThrThrPheCysLeu 85         95        105        115        125        135        145        155
GGATTCTGGGTGGTTAGAGTCACAAGAACCTGGGTTCCCAAAGGTCTGAAGAGTCCACCCGGACCCTGGGGCTTG
GlyPheTrpValValArgValThrArgThrTrpValProLysGlyLeuLysSerProProGlyProTrpGlyLeu 160        170        180        190        200        210        220        230
CCCTTCATAGGGCACGTGCTGACCCTGGGGAAGAACCACACTGTCACTGACAAAACTGAGTCAGTCAGCAGTATGGG
ProPheIleGlyHisValLeuThrLeuGlyLysAsnHisThrValThrAspLysThrGluSerValSerGlnTyrGly 235        245        255        265        275        285        295        305
GACGTGCTCCAGATCCCGTATTGGCTCCACACCCGTGGTGTGCTGAGCGGCCTGAACACCATCAAGCAGGCCCTG
AspValLeuGlnIleIleGlySerGlyGlySerThrProValValLeuSerGlyLeuAsnThrIleLysGlnAlaLeu 310        320        330        340        350        360        370        380
GTGAAACAGGGGGATGACTTCAAAGGCCGGCCAGACCTTCACAGCTTCACACTTATCGCTAATGGGCTAATGGGCAGAGCATG
ValLysGlnGlyAspAspPheLysGlyArgProAspLeuTyrSerPheThrLeuIleAlaAsnGlyGlnSerMet 385        395        405        415        425        435        445        455
ACTTTCAACCCAGACTCTGGGCCTGCCCTGGGGCTGCCCCAGAATGCCTGAAGAGTTTCTCC
ThrPheAsnProAspSerGlyProLeuTrpAlaAlaArgArgLeuAlaGlnAsnAlaLeuLysSerPheSer 460        470        480        490        500        510        520        530
ATAGCCCTCAGACCCAACACTGGCTCCTCTTGCTACTTGGAAGAGCACGTGAGCAAAGAGGCTGAATACTTAATC
IleAlaSerAspProThrLeuAlaSerSerCysTyrLeuGluGluHisValSerLysGluAlaGluTyrLeuIle
```

FIG. 3 (2)

```
         535                  545                  555                  565                  575                  585                  595                  605
AGCAAGTTCCAGAAGCTGATGGCAGAGGTTGCCACTTCGACCCTTTCAAGTATTGTTGGTGTCAGTGGCCAAT
SerLysPheGlnLysLeuMetAlaGluValGlyHisPheAspProPheLysTyrLeuValValSerValAlaAsn 610                  620                  630                  640                  650                  660                  670                  680
GTCATCTGTGCCATATGCTTTGGCAGACGTTATGACCAAGAGCTGCTCAGATAGTCATCAATCTAAGC
ValIleCysAlaIleCysPheGlyArgArgTyrAspHisAspGlnGluLeuLeuSerIleValAsnLeuSer 685                  695                  705                  715                  725                  735                  745                  755
AATGAGTTTGGGGAGGTTACTGGTTCTGGATACCCAGCTGACTTCATTCCTATCCTCCCGTTACCTCCCTAACTCT
AsnGluPheGlyGluValThrGlySerGlyTyrProAlaAspPheIleProIleLeuArgTyrLeuProAsnSer 760                  770                  780                  790                  800                  810                  820                  830
TCCCTGGATGCCTTCAAGGACTTGAATAAGAAGTTCTACAGTTTCATGAAGAAGTAATCAAAGAGCACTACAGG
SerLeuAspAlaPheLysAspLeuAsnLysLysPheTyrSerPheMetLysLysLeuIleLysGluHisTyrArg 835                  845                  855                  865                  875                  885                  895                  905
ACATTTGAGAAGGGCCACATCCGGGACATCACAGACAGCCTCATTGAGCATTGTCAGGACAGGAGGCTGGACGAG
ThrPheGluLysGlyHisIleArgAspIleThrAspSerLeuIleGluHisCysGlnAspArgArgLeuAspGlu 910                  920                  930                  940                  950                  960                  970                  980
AATGCCAATGTCCAGCTCTCAGATGATAAGGTCATTATTGACCTTCTTTGACCTTCTTTTGGAGCTGGGTTTGACACA
AsnAlaAsnValGlnLeuSerAspAspLysValIleThrIleValPheAspLeuPheGlyAlaGlyPheAspThr 985                  995                  1005                 1015                 1025                 1035                 1045                 1055
ATCACAACTGCTATCTCTTGGAGCCTCATGTACCTGGTAACCAACCCTAGGATACAGAGAAAGATCCAGGAGGAG
IleThrThrAlaIleSerTrpSerLeuMetTyrLeuValThrAsnProArgIleGlnArgLysIleGlnGluGlu
```

FIG. 3 (3)

```
              1060       1070       1080       1090       1100       1110       1120      1130
         TTAGACACAGTGATTGGCAGGGATCGGCAGCCCCGGCTTTCTGACAGACCTCAGTGCCCTATCTGGAGGCCTTC
         LeuAspThrValIleGlyArgAspArgGlnProArgLeuSerAspArgProGlnLeuProTyrLeuGluAlaPhe 1135       1145       1155       1165       1175       1185       1195      1205
         ATCCTGGAGACCTTCGACATTCATCCTTTGTCCCATTCCACCATCCCCACAGCACCATAAGAGATACAAGTCTG
         IleLeuGluThrPheAspIleHisProLeuSerHisSerThrIleProHisSerThrIleArgAspThrSerLeu 1210       1220       1230       1240       1250       1260       1270      1280
         AATGGCTTCTATATCCCCAAGGGACACTGTGTCTTTGTGAACCAGTGGCAGGTTAACCATGACCAGGAACTATGG
         AsnGlyPheTyrIleProLysGlyHisCysValPheValAsnGlnTrpGlnValAsnHisAspGlnGluLeuTrp 1285       1295       1305       1315       1325       1335       1345      1355
         GGTGATCCAAACGAGTTCCGGCCTGAAAGTTTCTTCTTAGCTTCCAGTGGCACTCTGGACAAACACCTGAGTGAGAAG
         GlyAspProAsnGluPheArgProGluArgPheLeuThrSerSerGlyThrLeuAspLysHisLeuSerGluLys 1360       1370       1380       1390       1400       1410       1420      1430
         GTCATTCTCTTTGGTTGGGCAAGCGAAAGTGCCATTGGCCGAGACCATTGGCCGACTGGAGGTCTTTCTCTTCCTG
         ValIleLeuPheGlyLeuGlyLysCysIleGlyThrIleGlyArgLeuGluValPheLeuPheLeu 1435       1445       1455       1465       1475       1485       1495      1505
         GCCATCTTGCTGCAGCAATGGAATTAATGTGTCCAGGCGAGAAGTGGATATGACTCCTGCCTATGGCTG
         AlaIleLeuLeuGlnLeuGlnMetGluPheAsnValSerProGlyGluLysValAspMetThrProAlaTyrGlyLeu 1510       1520       1530       1540       1550       1560       1570      1580
         ACTTTAAAACATGCCCGCTGTGAGCACTTCCAAGTGCAGATGCGGTCTTCTGGTCCTCGATCGGCTGCTGCTGCT
         ThrLeuLysHisAlaArgCysGluHisPheGlnValGlnMetArgSerSerGlyProArgSerAlaAlaAlaAla
```

FIG. 3(4)

```
         1585            1595            1605            1615            1625            1635            1645           1655
CGAGCCATGATCCAAACAACGGCCCCACCCGTCAAAGAGAGCAGCTTCGTGGAAAAGATGAAGAAAACGGGAAGG
ArgAlaMetIleGlnThrThrAlaProProValLysGluSerSerPheValGluLysMetLysLysThrGlyArg 1660            1670            1680            1690            1700            1710            1720           1730
AACATTATCGTATTCTATGGCTCCCAGACGGGAACCGGCTGAGGAGTTGCCAACCGGCTGTCCAAGGATGCCCAC
AsnIleIleValPheTyrGlySerGlnThrGlyThrAlaGluPheAlaAsnArgLeuSerLysAspAlaHis 1735            1745            1755            1765            1775            1785            1795           1805
CGGCTACGGGATGCGGGACATGTCCCAGAGTATGACTTGGCCCACCCTGAGCAGCAGCCTGCCTGAGATC
ArgTyrGlyMetArgGlyMetSerAlaAspProGluGluTyrAspLeuAlaAspLeuSerSerLeuProGluIle 1810            1820            1830            1840            1850            1860            1870           1880
GACAAGTCCCTGGTAGTCTTCTGCATGGCCACATACGGAGAGGGCCACCCCACGGACAATGCCCAGGACTTCTAT
AspLysSerLeuValValPheCysMetAlaThrTyrGlyGluGlyAspProThrAspAsnAlaGlnAspPheTyr 1885            1895            1905            1915            1925            1935            1945           1955
GACTGGCTGCAGGAGACTGACGTGGACCTCACTGGGGTCAAGTTTGCTGTATTTGGTCTTGGGAACAAGACCTAT
AspTrpLeuGlnGluThrAspValAspLeuThrGlyValLysPheAlaValPheGlyLeuGlyAsnLysThrTyr 1960            1970            1980            1990            2000            2010            2020           2030
GAGCACTTCAATGCCATGGGCAAGTATGTGGACCAGCGGCTGGAGCAGCTTGGCGCCCAGCGCATCTTTGAGTTG
GluHisPheAsnAlaMetGlyLysTyrValAspGlnArgLeuGluGlnLeuGlyAlaGlnArgIlePheGluLeu 2035            2045            2055            2065            2075            2085            2095           2105
GGCCTTGGTGATGATGACGGGAACTTGGAAGAGGATTTCATCACGTGGAGGGAGCAGTTCTGGCCAGCTGTCTGC
GlyLeuGlyAspAspAspGlyAsnLeuGluGluAspPheIleThrTrpArgGluGlnPheTrpProAlaValCys
```

FIG. 3(5)

```
         2110          2120          2130          2140          2150          2160          2170       2180
GAGTTCTTTGGGGTAGAAGCCACTGGGAGGAGGAGTCGAGCATTCGCCAGTATGAGCTCGTGGTCCACGAAGACATG
GluPhePheGlyValGluAlaThrGlyGluGluSerGlyGluSerIleArgGlnTyrGluLeuValHisGluAspMet 2185          2195          2205          2215          2225          2235          2245       2255
GACGTAGCCAAGGTGTACACGGGTGAGATGGGCCGTCTGAAGAGCTACGAGAACCAGAAACCCCCTTCGATGCT
AspValAlaLysValTyrThrGlyGluMetGlyArgLeuLysSerTyrGluAsnGlnLysProProPheAspAla 2260          2270          2280          2290          2300          2310          2320       2330
AAGAATCCATTCCTGGCTGCTGTCACCCGCCAACCGGAAGCTGAACCAAGGCACTGAGGGCATCTAATGCACCTG
LysAsnProPheLeuAlaAlaValThrAlaAsnArgLysLeuAsnGlnGlyThrGluArgHisLeuMetHisLeu 2335          2345          2355          2365          2375          2385          2395       2405
GAGTTGGACATCTCAGATCTCCAAGATCAGGTATGAATCTGGAGATCACCTGGCCTGTGTACCCAGCCAATGACTCA
GluLeuAspIleSerAspSerLysIleArgTyrGluSerGlyAspHisValAlaValTyrProAlaAsnAspSer 2410          2420          2430          2440          2450          2460          2470       2480
GCCCCTGGTCAACCAGATTGGGGAGATCCTGGGAGCTGACCTGGATGTCATCATGTCTCTAAACAATCTCGATGAG
AlaLeuValAsnGlnIleGlyGluIleLeuGlyAlaAspLeuAspValIleMetSerLeuAsnAsnLeuAspGlu 2485          2495          2505          2515          2525          2535          2545       2555
GAGTCAAACAAGAAGAAGCATCCGTTCCCCTGCCCCTACCCGACCACTGACTACTACCTGGACATACT
GluSerAsnLysLysHisProPheProCysProProThrThrTyrArgThrAlaLeuThrTyrLeuAspIleThr 2560          2570          2580          2590          2600          2610          2620       2630
AACCCGCCACGCCACCAATGTGCTCTACGAACTGGCACAGTACGCCCTCAGAGCCCTCGGAGCAGGAGCACCTGCAC
AsnProProArgThrAsnValLeuTyrGluLeuAlaGlnTyrAlaSerGluProSerGluGlnHisLeuHis
```

FIG. 3(6)

```
        2635      2645      2655      2665      2675      2685      2695      2705
AAGATGGCGTCATCCTCAGGCGAGGCAAGGAGCTGTACCTGAGCTGGGTGGTGGAAGCCCGGAGGCACATCCTA
LysMetAlaSerSerGlyGlyLysGluLeuTyrLeuSerTrpValValGluAlaArgArgHisIleLeu 2710      2720      2730      2740      2750      2760      2770      2780
GCCATCCTCCAAGACTACTACCATCGCGGGCCACCACCACTCGACCACCCTGTGTGAGCTGCTGCCACGCCTGCAGGCC
AlaIleLeuGlnAspTyrProSerLeuArgProProIleAspHisLeuCysGluLeuLeuProArgLeuGlnAla 2785      2795      2805      2815      2825      2835      2845      2855
CGATACTACTCCATTGCCTCATCCTCCAAGGTCCACAACTCCGTGCACATCTGTGCCGTGGCCGTGGAGTAC
ArgTyrTyrSerIleAlaSerSerLysValHisProAsnSerValHisIleCysAlaValAlaValGluTyr 2860      2870      2880      2890      2900      2910      2920      2930
GAAGCGAAGTCTGGCCGAGTGAACAAGGGGGTGGCCACTAGCTGGCTTCGGGCCAAGGACCAGGCGAGAAT
GluAlaLysSerGlyArgValAsnLysGlyValAlaThrSerTrpLeuArgAlaLysGluProAlaGlyGluAsn 2935      2945      2955      2965      2975      2985      2995      3005
GGCGGCCGCGGCCCCTGGTACCCCATGTTCGTGCGCAAATCTCAGTTCCGCTTGCCTTCAAGTCCACCACCTGTC
GlyGlyArgAlaAlaLeuValProMetPheValArgLysSerGlnPheArgLeuProPheLysSerThrThrProVal 3010      3020      3030      3040      3050      3060      3070      3080
ATCATGGTGGGCCCCGGCACTGGGATTGCCCCTTTCATGGGCTTCATCCAGGAACGAGCTTGGCTTCGAGAGCAA
IleMetValGlyProGlyThrGlyIleAlaProPheMetGlyPheIleGlnGluArgAlaTrpLeuArgGluGln 3085      3095      3105      3115      3125      3135      3145      3155
GGCAAGGAGTGGGAGAGACGCTGTACTATGGCTGCCGGCCTCGGATGAGGACTATCTGTACCGTGAAGAG
GlyLysGluValGlyGluThrLeuLeuTyrTyrGlyCysArgArgSerAspTyrLeuTyrArgGluGlu
```

FIG. 3 (7)

```
       3160        3170        3180        3190        3200        3210        3220       3230
CTAGCCCGGCTTCCACAAGGACGGTGCCCTCACGGCAGCTTAATGTGGCCCTTTCCCGGGAGCAGGCCCACAAGGTC
LeuAlaArgPheHisLysAspGlyAlaLeuThrGlnLeuAsnValAlaPheSerArgGluGlnAlaHisLysVal 3235        3245        3255        3265        3275        3285       3295       3305
TATGTCCAGCACCTTCTGAAGAGACAGGGAAACACCTGTGGAAGCTGATCCACGAGGGCGGTGCCACATCTAT
TyrValGlnHisLeuLeuLysArgAspArgGluHisLeuTrpLysLeuIleHisGluGlyAlaHisIleTyr 3310        3320        3330        3340        3350       3360       3370       3380
GTGTGCGGGGATGCTGCGAAATATGGCCAAAGATGTGCAAAACACATTCTATGACAATTCTGTGGCTGAGTTCGGGCCC
ValCysGlyAspAlaArgAsnMetAlaLysAspValGlnAsnThrPheTyrAspIleValAlaGluPheGlyPro 3385        3395        3405        3415        3425       3435       3445       3455
ATGGAGCACACCCAGGCTGTGGACTATGTTAAGAAGCTGATGACCAAGGGCCGCTACTACTAGATGTGTGGAGC
MetGluHisThrGlnAlaValAspTyrValLysLysLeuMetThrLysGlyArgTyrSerLeuAspValTrpSer
```

TAG
***

F I G. 4 (1)

```
         10                 20                 30                 40                 50                 60                 70                 80
ATGCCTTCTGTGTATGGATTCCCAGCTTCACATCAGCCACAGAGCTGCTCCTGCCCGTCACCACATTCTGCCTT
MetProSerValTyrGlyPheProAlaPheThrSerAlaThrGluLeuLeuLeuAlaValThrThrPheCysLeu 85                 95                105                115                125                135                145               155
GGATTCTGGGTGGTTAGAGTCACAAGAACCTGGGTTCCCAAAGGTCTGAAGAGTCCACCCGGACCCTGGGGCTTG
GlyPheTrpValValArgValThrArgThrTrpValProLysGlyLeuLysSerProProGlyProTrpGlyLeu 160                170                180                190                200                210                220                230
CCCTTCATAGGGCACGTGCTGACCCTGGGGAAGAACCCACACCACCTGTCACTGACAAAACTGAGTCAGCAGTATGGG
ProPheIleGlyHisValLeuThrLeuGlyLysAsnProHisLeuSerLeuThrLysLeuSerGlnGlnTyrGly 235                245                255                265                275                285                295                305
GACGTGCTGCAGATCCGTATTGGCTCCACACCCGTGGTGCTGAGCGGCCTGAACACCATCAAGCAGGCCCTG
AspValLeuGlnIleArgIleGlySerThrProValValLeuSerGlyLeuAsnThrIleLysGlnAlaLeu 310                320                330                340                350                360                370                380
GTGAAACAGGGGATGACTTCAAAGGCCGGCCAGACCTTCACACTTATCGCTAATGGCCAGAGCATG
ValLysGlnGlyAspAspPheLysGlyArgProAspLeuTyrSerPheThrLeuIleAlaAsnGlyGlnSerMet 385                395                405                415                425                435                445                455
ACTTTCAACCCAGACTCTGGACCCCGTCTGCCCCCGGCCCGGCCCCAGAATGCGCTGAAGTTTCTCC
ThrPheAsnProAspSerGlyProLeuTrpAlaAlaArgArgLeuAlaGlnAsnAlaLeuLysSerPheSer 460                470                480                490                500                510                520                530
ATAGCCTCAGACCCAACACTGGCATCCTCTTGCTACTTGGAAGAGCACGTGAGCAAAGAGGCTGAATACTTAATC
IleAlaSerAspProThrLeuAlaSerSerCysTyrLeuGluGluHisValSerLysGluAlaGluTyrLeuIle
```

FIG. 4 (2)

```
        535            545            555            565            575            585            595          605
AGCAAGTTCCAGAAGCTGATGGCAGAGGTTGGCCACTTCGACCCTTTCAAGTATTGTGGTGTTCAGTGGCCAAT
SerLysPheGlnLysLeuMetAlaGluValGlyHisPheAspProPheLysTyrLeuValValSerValAlaAsn 610            620            630            640            650            660            670          680
GTCATCTGTGCCATATGCTTTGGCAGACGTTATGACGACCAAGAGCTGCTCAGCATAGTCAATCTAAGC
ValIleCysAlaIleCysPheGlyArgArgTyrAspHisAspGlnGluLeuLeuSerIleValAsnLeuSer 685            695            705            715            725            735            745          755
AATGAGTTTGGGGAGGTTACTGGTTCTGGATACCCAGCTGACTTCATTCCTATCCTCCGTTACCTCCCTAACTCT
AsnGluPheGlyGluValThrGlySerGlyTyrProAlaAspPheIleProIleLeuArgTyrLeuProAsnSer 760            770            780            790            800            810            820          830
TCCCTGGATGCCTTCAAGGACTTGAATAAGAAGTTCTACAGTTTCATGAAGAAGCTAATCAAAGAGCACTACAGG
SerLeuAspAlaPheLysAspLeuAsnLysLysPheTyrSerPheMetLysLysLeuIleLysGluHisTyrArg 835            845            855            865            875            885            895          905
ACATTTGAGAAGGGCCACATCCGGGACATCACAGACAGCCTCATTGAGCATTGTCAGGACAGGAGGCTGGACGAG
ThrPheGluLysGlyHisIleArgAspIleThrAspSerLeuIleGluHisCysGlnAspArgArgLeuAspGlu 910            920            930            940            950            960            970          980
AATGCCAATGTCCAGCTCTCAGATGATAAGGTCATTACGATTGTTTTGACCTCTTTGAGCTGGGTTTGACACA
AsnAlaAsnValGlnLeuSerAspAspLysValIleThrIleValPheAspLeuPheAlaGlyPheAspThr 985            995            1005           1015           1025           1035           1045         1055
ATCACAACTGCTATCTCTTGGAGCCTCATGTACCTGGTAACCAACCCTAGGATACAGAGAAAGATCCAGGAGGAG
IleThrThrAlaIleSerTrpSerLeuMetTyrLeuValThrAsnProArgIleGlnArgLysIleGlnGluGlu
```

FIG. 4 (3)

```
1060            1070            1080            1090            1100            1110            1120            1130
TTAGACACAGTGATTGGCAGGATCGGCAGCCCCGGCTTTCTGACAGACCTCAGCTGCCCTATCTGGAGGCCTTC
LeuAspThrValIleGlyArgAspArgGlnProArgLeuSerAspArgProGlnLeuProTyrLeuGluAlaPhe 1135            1145            1155            1165            1175            1185            1195            1205
ATCCTGGAGACCTTCGACATTCATCCTTTGTCCCATTCACCATCCCCACAGCACCATAAGAGATACAAGTCTG
IleLeuGluThrPheAspIleHisProPheSerProHisSerProThrIleArgAspThrIleArgAspThrSerLeu 1210            1220            1230            1240            1250            1260            1270            1280
AATGGCTTCTATATCCCCAAGGGACACTGTGTCTTTGTGAACCAGTGGCAGGTTAACCATGACCAGGAACTATGG
AsnGlyPheTyrIleProLysGlyHisCysValPheValAsnGlnTrpGlnValAsnHisAspGlnGluLeuTrp 1285            1295            1305            1315            1325            1335            1345            1355
GGTGATCCCAAACGAGTTCCGGGCCCTGAAAGGTTTCTTCCAGTGGCACTCTGGACAAACACCTGAGTGAGAAG
GlyAspProAsnGluPheArgProGluArgPheLeuThrSerSerGlyThrSerSerGlyThrLeuAspLysHisLeuSerGluLys 1360            1370            1380            1390            1400            1410            1420            1430
GTCATTCTCTTTGGTTTGGCCAAGGCGAAAGTGCATTGGGCAGACCATTGGGCGAGCTCTTTCTCTTCCTG
ValIleLeuPheGlyLeuGlyLysAlaLysCysIleGlyGluThrIleGlyArgLeuGluValPheLeuPheLeu 1435            1445            1455            1465            1475            1485            1495            1505
GCCATCTGCTGCTGCAGCAAATGGAATTTAATGTCTCACCAGGCGAGAAGGTGGATATGACTCCTGCCTATGGCCTG
AlaIleLeuLeuGlnMetGluPheAsnValSerProGlyLysValAspMetThrProAlaTyrGlyLeu 1510            1520            1530            1540            1550            1560            1570            1580
ACTTTAAAACATGCCTGCTGCGAGCACTTCCAAGTGCAGATGCGGCTCTTCCTGGTCCTGATCGGCTGCTGCTGCT
ThrLeuLysHisAlaArgCysGluHisPheGlnValMetArgSerSerGlyProArgSerAlaAlaAlaAla
```

FIG. 4 (4)

```
                1585      1595      1605      1615      1625      1635      1645      1655
           CGATCGGCTGCTGCTCGATCGGCTGCTGCTCGAGCCATGATCCAAACAACGGCCCCACCCGTCAAAGAG
           ArgSerAlaAlaAlaArgSerAlaAlaAlaArgAlaAlaMetIleGlnThrThrAlaProProValLysGlu 1660      1670      1680      1690      1700      1710      1720      1730
  AGCAGCTTCGTGGAAAAGATGAAGAAAACGGGAAGGAACATTATCGTATTCTATGGCTCCCAGACGGGAACCGCT
  SerSerPheValGluLysMetLysLysThrGlyArgAsnIleIleValPheTyrGlySerGlnThrGlyThrAla 1735      1745      1755      1765      1775      1785      1795      1805
       GAGGAGTTTGCCAACCGGCTGTCCAAGGATGCCCACCGGATGCGGGGCATGCGCCAGACCCTGAAGAG
       GluGluPheAlaAsnArgLeuSerLysAspAlaHisArgMetArgGlyMetSerAlaAspProGluGlu 1810      1820      1830      1840      1850      1860      1870      1880
       TATGACTTGGCCGACCTGAGCAGCCTGCCTGAGATCGACAAGTCCCTGGTAGTCTTCTGCATGGCCACATACGGA
       TyrAspLeuAlaAspLeuSerSerLeuProGluIleAspLysSerLeuValValPheCysMetAlaThrTyrGly 1885      1895      1905      1915      1925      1935      1945      1955
       GAGGGCGACCCCACGGACAATGCGGACTTCTATGACTGGCTGCAGGAGACTGGACGTGGACCTCACTGGGGTC
       GluGlyAspProThrAspAsnAlaGlnAspPheTyrAspTrpLeuGlnGluThrAspValAspLeuThrGlyVal 1960      1970      1980      1990      2000      2010      2020      2030
       AAGTTTGCTGTATTTGGTCTTGGGAACAAGACCTATGAGCACTTCAATGCCATGGGCAAGTATGTGGACCAGCGG
       LysPheAlaValPheGlyLeuGlyAsnLysThrTyrGluHisPheAsnAlaMetGlyLysTyrValAspGlnArg 2035      2045      2055      2065      2075      2085      2095      2105
       CTGGAGCAGCTTGGGGCCCAGCCCATCTTTGAGTTGGGCCTTGCTGATGACGGAACTTGGAAGAGGATTTC
       LeuGluGlnLeuGlyAlaGlnArgIlePheGluLeuGlyLeuGlyAspAspGlyAsnLeuGluAspPhe
```

FIG. 4 (5)

```
         2110       2120       2130       2140       2150       2160       2170      2180
ATCACGTGGAGGGAGGAGCAGTTCTGGCCAGCTGTGTGCGAGTTCTTTGGGTAGAAGCCACTGGGGAGGAGTCGAGC
IleThrTrpArgGluGlnPheTrpProAlaValCysGluPhePheGlyValGluAlaThrGlyGluGluSerSer 2185       2195       2205       2215       2225       2235       2245     2255
ATTCGCCAGTATGAGCTCGTGGTCCACGAAGACATGGACTAGCCAAGGTGTACACGGGTGAGATGGGCCGTCTG
IleArgGlnTyrGluLeuValValHisGluAspMetAspValAlaLysValTyrThrGlyGluMetGlyArgLeu 2260       2270       2280       2290       2300       2310       2320     2330
AAGAGCTACGAGAACCAGAACCCCCTTCGATGCTAAGAATCCATTCCTGGCTGTCACCGCCAACCGGAAG
LysSerTyrGluAsnGlnLysProProPheAspAlaLysAsnProPheLeuAlaAlaValThrAlaAsnArgLys 2335       2345       2355       2365       2375       2385       2395     2405
CTGAACCAAGGCACTGAGCGGCATCTAATGCACCTGGAGTTGGACATCTCAGACTCCAAGATCAGTATGAATCT
LeuAsnGlnGlyThrGluArgHisLeuMetHisLeuGluLeuAspIleSerAspSerLysIleArgTyrGluSer 2410       2420       2430       2440       2450       2460       2470     2480
GGAGATCACGTGGCTGTGTACCCAGCCAATGACTACCCTGGTCAACCAGATTGGGAGGAGATCCTGGGAGCTGAC
GlyAspHisValAlaValTyrProAlaAsnAspSerAlaLeuValAsnGlnIleGlyGluIleLeuGlyAlaAsp 2485       2495       2505       2515       2525       2535       2545     2555
CTGGATGTCATCATGTCTCTAAACAATTCCGATGAGGAGTCAAACAAGAAGCATCCGTTCCCTGCCCCACCACC
LeuAspValIleMetSerLeuAsnAsnLeuAspGluGluSerAsnLysLysHisProPheProCysProThrThr 2560       2570       2580       2590       2600       2610       2620     2630
TACCGCACGGCCCTCACCTGGACATCACTAACCCGACGCACCAATGTGCTCTACGAACTGGAACTGGCACAG
TyrArgThrAlaLeuThrTyrTyrLeuAspIleThrAsnProArgThrAsnValLeuTyrGluLeuAlaGln
```

FIG. 4 (6)

```
        2635       2645       2655       2665       2675       2685       2695   2705
    TACGCCCTCAGAGCCCTCGGAGCAGGAGCACCTGCACAAGATGGCGTCATCCTCAGGCGGAGGGCAAGGAGCTGTAC
    TyrAlaSerGluProSerGluGlnGluHisLeuHisLysMetAlaSerSerGlyGluGlyLysGluLeuTyr 2710       2720       2730       2740       2750       2760       2770  2780
    CTGAGCTGGTGGTGGCAGAAGCCCGGAGGCACATCCTAGCCATCCTCCAAGACTACCATCACTGCGGGCCACCCATC
    LeuSerTrpValValGlyAlaArgArgHisIleLeuAlaIleLeuGlnAspTyrProSerLeuArgProProIle 2785       2795       2805       2815       2825       2835       2845  2855
    GACCACCTGTGCGAGCTGCTGCCAGGGCCCTGCAGGGCCCGATACTACTCCATTGCCTCATCCTCCAAGGTCCACCCC
    AspHisLeuCysGluLeuLeuProArgLeuGlnAlaArgTyrTyrSerIleAlaSerSerLysValHisPro 2860       2870       2880       2890       2900       2910       2920  2930
    AACTCCGTGCACATCTGTGCCGCTGGCCGTGGAGTACGAAGGCGAAGTCTGGGCCGAGTGAACAAGGGGGTGGCCACT
    AsnSerValHisIleCysAlaAlaValGluTyrGluAlaValGluTyrGluAlaLysSerGlyArgValAlaAsnLysGlyValAlaThr 2935       2945       2955       2965       2975       2985       2995  3005
    AGCTGGCTTCGGGCCAAGGAACCAGCAGGCGAGAATGGCGCGCCCTGGTACCCATGGCCGCTGGAGCGAGCCACCATGTTCGTGCGCAAATCT
    SerTrpLeuArgAlaLysGluProAlaGlyGluAsnGlyGlyArgAlaLeuValProMetPheValArgLysSer 3010       3020       3030       3040       3050       3060       3070  3080
    CAGTTCCGGCTTGCCTTCAAGTCCACCACACTGTCATCATGGTGGGCCCCGGCACTGGGGATTGCCCCTTTCATG
    GlnPheArgLeuProPheLysSerThrThrProValIleMetValGlyProGlyThrGlyIleAlaProPheMet 3085       3095       3105       3115       3125       3135       3145  3155
    GGCTTCATCCAGGAACGAGCTTGGCTTCGAGAGCAAGGAGGTGGGAGAGACGCTGCTATACTATGGCTGC
    GlyPheIleGlnGluArgAlaTrpLeuArgGluArgGluValGlyGluValGlyLysGluThrLeuLeuTyrTyrGlyCys
```

FIG. 4 (7)

```
      3160      3170      3180      3190      3200      3210      3220      3230
CGGCGCTGGATGAGGACTATCTGTACCGTGAAGAGCTAGCCGTTCCACAAGGACGGTGCCCTCACGCAGCTT
ArgArgSerAspGluAspTyrLeuTyrArgGluGluLeuAlaArgPheHisLysAspGlyAlaLeuThrGlnLeu 3235      3245      3255      3265      3275      3285      3295      3305
AATGTGGCCTTTTCCCGGGAGCAGGCCCACAAGGTCTATGTCCAGCACCTTCTGAAGAGACAGGGAACACCTG
AsnValAlaPheSerArgGluGlnAlaHisLysValTyrValGlnHisLeuLeuLysArgAspArgGluHisLeu 3310      3320      3330      3340      3350      3360      3370      3380
TGGAAGCTGATCCACGAGGGCGGTGCCCACATCTATGTGTGCGGGGATGCTCGAAATATGGCCAAAGATGTGCAA
TrpLysLeuIleHisGluGlyGlyAlaHisIleTyrValCysGlyAspAlaArgAsnMetAlaLysAspValGln 3385      3395      3405      3415      3425      3435      3445      3455
AACACATTCTATGACATTGTGGCTGAGTTCCGGCCCATGGAGCACACCCAGGCTGTGGACTATGTTAAGAAGCTG
AsnThrPheTyrAspIleValAlaGluPheGlyProMetGluHisThrGlnAlaValAspTyrValLysLysLeu 3460      3470      3480      3490
ATGACCAAGGGCCGCTACTACTAGATGTGTGGAGCTAG
MetThrLysGlyArgTyrSerLeuLeuAspValTrpSer***
```

FIG. 5(1)

```
        10         20         30         40         50         60         70         80
ATGCCTTCTGTGTATGGATTCCCAGCCTTCACATCAGCCACCAGAGCTGCTCCTGCCCGTCACCACATTCTGCCTT
MetProSerValTyrGlyPheProAlaPheThrSerAlaThrGluLeuLeuLeuAlaValThrThrPheCysLeu 85         95        105        115        125        135        145        155
GGATTCTGGGTGGTTAGAGTCAAGAGAACCTGGGTTCCCAAAGGTCTGAAGAGTCCACCCGGACCTGGGGGCTTG
GlyPheTrpValValArgValThrArgThrTrpValProLysGlyLeuLysSerProProGlyProTrpGlyLeu 160        170        180        190        200        210        220        230
CCCTTCATAGGGCACGTGCTGCTGACCCTGGGGAAGAACCCACACCTGTCACTGACAAAACTGAGTCAGGAGTATGGG
ProPheIleGlyHisValLeuThrLeuGlyLysAsnProHisLeuSerLeuThrLysLeuSerGlnGlnTyrGly 235        245        255        265        275        285        295        305
GACGTGCTGCAGATCCGTATTGGCTCCTCCACACCCGTGGTTGTTCTGAGCGGCCTGAGCGGCCTGAACCAGGCCCTG
AspValLeuGlnIleArgIleGlySerThrProValValLeuSerGlyLeuAsnThrIleLysGlnAlaLeu 310        320        330        340        350        360        370        380
GTGAAACAGGGGATGACTTCAAAGGGCCGGATGCCAGACTTCACACTTATCGCTAATGGCCAGAACGGCAGAGCATG
ValLysGlnGlyAspAspPheLysGlyArgProAspLeuTyrSerPheThrLeuIleAlaAsnGlyGlnSerMet 385        395        405        415        425        435        445        455
ACTTTCAACCTCGACCCTGGGCCTGTGCCCGCCCTGGCCCCAGAATGCCTGAAGAGTTTCTCC
ThrPheAsnProAspSerGlyProLeuTrpAlaAlaArgArgLeuAlaGlnAsnAlaLeuLysSerPheSer 460        470        480        490        500        510        520        530
ATAGCCTCAGACCCAACACTGGCATCCTCTGCTACTTGGAAGAGCACGTGAGCAAAGAGGCTGAATACTTAATC
IleAlaSerAspProThrLeuAlaSerSerCysTyrLeuGluGluHisValSerLysGluAlaGluTyrLeuIle
```

FIG. 5 (2)

```
        535            545            555            565            575            585            595           605
AGCAAGTTCCAGAAGCTGATGGCAGAGGTTGGCCACTTGGCCTTCGACCCTTTCAAGTATTGGTGGTGTCAGTGGCCAAT
SerLysPheGlnLysLeuMetAlaGluValGlyHisPheAspProPheLysTyrLeuValValSerValAlaAsn 610            620            630            640            650            660            670           680
GTCATCTGTGCCATATGCTTTGGCAGACGTTATGACCACGAGACTGCTCAGCAGATAGTCAATCTAAGC
ValIleCysAlaIleCysPheGlyArgArgTyrAspHisAspGlnGluLeuLeuSerIleValAsnLeuSer 685            695            705            715            725            735            745           755
AATGAGTTTGGGGAGGTTACTGGTTCTGGATACCCAGCTGACTTCATTCCTATCCTCCGTTACCTCCCTAACTCT
AsnGluPheGlyGluValThrGlySerGlyTyrProAlaAspPheIleProIleLeuArgTyrLeuProAsnSer 760            770            780            790            800            810            820           830
TCCCTGGATGCCTTCAAGGACTTGAATAAGAAGTTCTACAGTTTCATGAAGAAGCTAATCAAAGAGCACTACAGG
SerLeuAspAlaPheLysAspLeuAsnLysLysPheTyrSerPheMetLysLysLeuIleLysGluHisTyrArg 835            845            855            865            875            885            895           905
ACATTTGAGAAGGGCCACATCCCGGGACATCACAGACAGCCTCATTGAGCATTGTCAGGATAGAAGGCTGGACGAG
ThrPheGluLysGlyHisIleArgAspIleThrAspSerLeuIleGluHisCysGlnAspArgArgLeuAspGlu 910            920            930            940            950            960            970           980
AATGCCAATGTCCAGCTCTCAGATGATAAGGTCATTACGATTGTTTTGACCTCTTTGGAGCTGGGTTTGACACA
AsnAlaAsnValGlnLeuSerAspAspLysValIleThrIleValPheAspLeuPheGlyAlaGlyPheAspThr 985            995            1005           1015           1025           1035           1045          1055
ATCACAACTGCTATCTCTTGGAGCCTCATGTACCTGGTAACCAACCCTAGGATACAGAGAAAGATCCAGGAGGAG
IleThrThrAlaIleSerTrpSerLeuMetTyrLeuValThrAsnProArgIleArgLysIleGlnGluGlu
```

FIG. 5 (3)

```
         1060        1070        1080        1090       1100       1110        1120       1130
TTAGACACAGTGATTGGCAGGGATCGGCAGCCCCCGGCTTTCTGACAGACCTCAGCTGCCTATCTGGAGGCCTTC
LeuAspThrValIleGlyArgAspArgGlnProArgLeuSerAspArgProGlnLeuProTyrLeuGluAlaPhe 1135        1145        1155        1165       1175       1185        1195       1205
ATCCTGGAGACCTTCCGACATTCATCCTTTGTCCCATTCACCATCCCCACAGCACCATAAGAGATACAAGTCTG
IleLeuGluThrPheArgHisSerSerPheValProPheThrIleProHisSerThrIleArgAspThrSerLeu 1210        1220        1230        1240       1250       1260        1270       1280
AATGGCTTCTATATCCCCAAGGGACACTGTCTTTGTGAACCAGTGGCAGGTTAACCATGGAGGAACTATGG
AsnGlyPheTyrIleProLysGlyHisCysValPheValAsnGlnTrpGlnValAsnHisAspGlnLeuTrp 1285        1295        1305        1315       1325       1335        1345       1355
GGTGATCCAAACGAGTTCCGGCCCTGAAAGGTTTCATTACCTCCAGTGCACTCTGGACAAACACCTGAGTGAGAAG
GlyAspProAsnGluPheArgProGluPheLeuThrSerSerGlyThrLeuAspLysHisLeuSerGluLys 1360        1370        1380        1390       1400       1410        1420       1430
GTCATTCTCTTTGGTTGGGCAAGGCAAATGGCATTGGGGAGACCATTGGCCGACTGGAGGTCTTCTCTCTG
ValIleLeuPheGlyLeuGlyLysGlnMetAlaLeuGlyGluThrIleGlyArgLeuGluValPheLeuPheLeu 1435        1445        1455        1465       1475       1485        1495       1505
GCCATCTCTGCTGCAGCAAATGGAATTTAATGTGTCACCAGGCGAGAAGTGGATATGACTCCTGCCTATGGCTG
AlaIleLeuLeuGlnMetGluPheAsnValSerProGlyGluLysValAspMetThrProAlaTyrGlyLeu 1510        1520        1530        1540       1550       1560        1570       1580
ACTTTAAAACATGCCCGCTGTGAGCACTTCCAAGTGCAGATGCGCTTCCTGGTCCTGAGCAGCAGCCGAT
ThrLeuLysHisAlaArgCysGluHisPheGlnValGlnMetArgSerSerGlyProArgAlaAlaAlaAlaAsp
```

FIG. 5 (4)

```
           1585         1595         1605         1615         1625         1635         1645         1655
       CGAGCCATGATCCAAACAACGGCCCCACCCGTCAAAGAGAGCAGCTTCGTGGAAAAGATGAAGAAAACGGGAAGG
        ArgAlaMetIleGlnThrAlaProProValLysGluSerSerPheValGluLysMetLysLysThrGlyArg 1660         1670         1680         1690         1700         1710         1720         1730
       AACATTATCGTATTCTATGGCTCCCAGACCCGGGAACCCGCTGAGGAGTTTGCCAACCGGCTGTCCAAGGATGCCCAC
        AsnIleIleValPheTyrGlySerGlnThrGlyThrAlaGluPheAlaAsnArgLeuSerLysAspAlaHis 1735         1745         1755         1765         1775         1785         1795         1805
       CGCTACGGGATGCGGGGCATGTCCGCAGACCCTGAAGAGTATGACTTGGCCGACCTGAGCAGCCTGCCTGAGATC
        ArgTyrGlyMetArgGlyMetSerAlaAspProGluGluTyrAspLeuAlaAspLeuSerSerLeuProGluIle 1810         1820         1830         1840         1850         1860         1870         1880
       GACAAGTCCCTGGTAGTCTTCTGCATGGCCACATACGGAGAGGGCGACCCCACGGACAATGCCCAGGACTTCTAT
        AspLysSerLeuValValPheCysMetAlaThrTyrGlyGluGlyAspProThrAspAsnAlaGlnAspPheTyr 1885         1895         1905         1915         1925         1935         1945         1955
       GACTGGCTCCAGGAGACTGACGTGGACCTCAAGTTCTCTGTATTTGTCTTGGGAACAAGACCTATCTTTGAGTTG
        AspTrpLeuGlnGluThrAspValAspLeuLysPheAlaValPheGlyLeuGlyAsnLysThrTyr 1960         1970         1980         1990         2000         2010         2020         2030
       GAGCACTTCAATGCCATGGGCAAGTATGTGGACCAGCGGCTTGAGCAGCTTGGCGCCCAGGCCATCTTTGAGTTG
        GluHisPheAsnAlaMetGlyLysTyrValAspGlnArgLeuGluGlnLeuGlyAlaGlnAlaIlePheGluLeu 2035         2045         2055         2065         2075         2085         2095         2105
       GGCCTTGGTGATGATGACGGGAACTTGGAAGAGGATTTCATCACGTGGAGGGAGCAGTTCTGGCCAGCTGTGTGC
        GlyLeuGlyAspAspAspGlyAsnLeuGluGluAspPheIleThrTrpArgGluGlnPheTrpProAlaValCys
```

FIG. 5 (5)

```
       2110       2120       2130       2140       2150       2160       2170       2180
GAGTCTCTTTGGGTAGAAGCCACTGGGAGGAGTCCAGCATTCGCCAGTATGAGCTCCTGGTCCACGAAGACATG
GluPhePheGlyValGluAlaThrGlyGluGluSerSerIleArgGlnTyrGluLeuValHisGluAspMet 2185       2195       2205       2215       2225       2235       2245       2255
GACGTAGCCAAGGTGTACACGGGTGAGATGGGCCGTCTGAAGAGCTACGAGAACCCCCCTTCGATGCT
AspValAlaLysValTyrThrGlyGluMetGlyArgLeuLysSerTyrGluAsnGlnLysProProPheAspAla 2260       2270       2280       2290       2300       2310       2320       2330
AAGAATCCATTCCTGCTGTCACCGCCAACCGGAAGCTGAACAAGGCACTGAGGGCATCTAATGCACCTG
LysAsnProPheLeuLeuAlaAlaValThrAlaAsnArgLysLeuAsnGlnGlyThrGluArgHisLeuMetHisLeu 2335       2345       2355       2365       2375       2385       2395       2405
GAGTTGGACATCTCAGATCTCCAAGATCAGGTATGAATCTGGAGATCACGTGGCTGTGTACCCAGCCAATGACTCA
GluLeuAspIleSerAspSerLysIleArgTyrGluSerGlyAspHisValAlaValTyrProAlaAsnAspSer 2410       2420       2430       2440       2450       2460       2470       2480
GCCCTGGTCAACCAGATTGGGGAGATCCTGGGAGCTGACCTGGATGTCATCATGTCTAAACAATCTCGATGAG
AlaLeuValAsnGlnIleGlyGluIleLeuGlyAlaAspLeuAspValIleMetSerLeuAsnAsnLeuAspGlu 2485       2495       2505       2515       2525       2535       2545       2555
GAGTCAAACAAGAAGCATCCGTTCCCCTGCCCCTACCGGCCCCTCACCTACTACCTGGACATCACT
GluSerAsnLysLysHisProPheProCysProThrThrTyrArgThrAlaLeuThrTyrTyrLeuAspIleThr 2560       2570       2580       2590       2600       2610       2620       2630
AACCCGGCCACGCCACCAATGTGCTCTACGAACTGGCACAGTACGGCCCTCAGAGCCCTCGGAGGAGGACCCTGCAC
AsnProProArgThrAsnValLeuTyrGluLeuAlaGlnTyrAlaSerGluProSerGluGlnHisLeuHis
```

FIG. 5(6)

```
         2635      2645      2655      2665      2675      2685      2695      2705
      AAGATGGGTCATCCTCAGGGAGGCAAGGAGCTGTACCTGAGCTGGTGGAAGCCCGGAGGCACATCCTA
      LysMetAlaSerSerGlyGluGluLysGluLeuTyrLeuSerTrpValValGluAlaArgArgHisIleLeu 2710      2720      2730      2740      2750      2760      2770      2780
      GCCATCCTCCAAGACTACTACCCATCACTGCGGCCACCCATCGACGACCTGTGTGAGCCTGTGCCACGCCTGCAGGCC
      AlaIleLeuGlnAspTyrProSerLeuArgProProIleAspHisLeuCysGluLeuLeuProArgLeuGlnAla 2785      2795      2805      2815      2825      2835      2845      2855
      CGATACTACTCCATTCCTGCCTCATCCTCCAAGGTCCACCCCAACTCCGTGCACATCTGTGCCGTGGCCCTGGAGTAC
      ArgTyrTyrSerIleAlaSerSerLysValHisProAsnSerValHisIleCysAlaValAlaValGluTyr 2860      2870      2880      2890      2900      2910      2920      2930
      GAAGGAAGTCTGGCCGAGTGAACAAGGGGTGCCACTAGCTGTCCGGCCCAAGGAACCAGGCCAGCAGGCGAGAAT
      GluAlaLysSerGlyArgValAlaAsnLysGlyValAlaAlaThrSerTrpLeuArgAlaLysGluProAlaGlyGluAsn 2935      2945      2955      2965      2975      2985      2995      3005
      GGGCGCCCGGCCCCTGGTACCCATGTCTTCGTGCGCCAAATCTCAGTTCCGCTTGTGCCTTTCAAGTCCACCACCTGTC
      GlyGlyArgAlaLeuValProMetPheValArgLysSerGlnPheArgPheLysProPheLysSerThrThrProVal 3010      3020      3030      3040      3050      3060      3070      3080
      ATCATGGTGGGCCCCGGCCACTGGGATTGCCCCTTTCATGGGCTTCATCCAGGAACGAGAGCTTGGCTTGAGAGCAA
      IleMetValGlyProGlyThrGlyIleAlaProPheMetGlyPheIleGlnGluArgAlaTrpLeuArgGluGln 3085      3095      3105      3115      3125      3135      3145      3155
      GGCAAGGAGGTGGGAGAGACGCTGCTATACTATGGCTGCCGGGATGAGGACTATCTGTACCGTGAAGAG
      GlyLysGluValGlyGluThrLeuLeuTyrTyrGlyCysArgArgSerAspTyrLeuTyrArgGluGlu
```

FIG. 5 (7)

```
        3160      3170      3180      3190      3200      3210      3220       3230
CTAGCCCCGCTTCCACAAGGACGGTGCCCTCACGGCAGCTTAATGTGGCCTTTTCCCGGGAGCAGGCCCACAAGGTC
LeuAlaArgPheHisLysAspGlyAlaLeuThrGlnLeuAsnValAlaPheSerArgGluGlnAlaHisLysVal 3235      3245      3255      3265      3275      3285      3295       3305
TATGTCCAGCACCTTCTGAAGAGAGACAGGGAACACCTGTGGAAGCTGATCCACGAGGCCGGTGCCCACATCTAT
TyrValGlnHisLeuLeuLysArgAspArgGluHisLeuTrpLysLeuIleHisGluGlyAlaHisIleTyr 3310      3320      3330      3340      3350      3360      3370       3380
GTGTGCGGGGATGCTCGAAATATGGCCAAAGATGTGCAAAACACATTCTATGACATTGTGGCTGAGTTCGGGCCC
ValCysGlyAspAlaArgAsnMetAlaLysAspValGlnAsnThrPheTyrAspIleValAlaGluPheGlyPro 3385      3395      3405      3415      3425      3435      3445       3455
ATGGAGCACACCCAGGCTGTGGACTATGTTAAGAAGCTGATGACCAAGGGCCGCTACTACTAGATGTGTGGAGC
MetGluHisThrGlnAlaValAspTyrValLysLysLeuMetThrLysGlyArgTyrSerLeuAspValTrpSer
```

TAG
***

FIG. 6(1)

```
         10         20         30         40         50         60         70         80
ATGCCTTCTGTGTATGGATTCCCAGCCTTCACATCAGCTGCTCCTGGCCCTGCTCCTGGCCCTCACCACATTCTGCCTT
MetProSerValTyrGlyPheProAlaPheThrSerAlaPheThrSerAlaThrGluLeuLeuLeuAlaValThrThrPheCysLeu 85         95        105        115        125        135        145        155
GGATTCTGGGTGGTTAGAGTCACAAGAACCTGGGTTCCCAAAGGTCTGAAGAGTCCACCCGGACCCTGGGGCTG
GlyPheTrpValValValArgValThrArgThrTrpValProLysGlyLeuLysSerProProGlyProGlyLeu 160        170        180        190        200        210        220        230
CCCTTCATAGGGCACGTGCTGACCCTGGGGAAGAACCCACACCTGTCACTGACAAAACTGAGTCAGCAGTATGGG
ProPheIleGlyHisValLeuThrLeuGlyLysAsnProHisLeuSerLeuThrLysLeuSerGlnGlnTyrGly 235        245        255        265        275        285        295        305
GACGTGCTGCAGATCCGTATTGGCTCCCACACCCGTGGTGTGCTGAGCGGCCTGAACACCATCAAGCAGCCCTG
AspValLeuGlnIleArgIleGlySerHisThrProValValLeuSerGlyLeuAsnThrIleLysGlnAlaLeu 310        320        330        340        350        360        370        380
GTGAAACAGGGGGATGACTTCAAAGGCCGGCCAGACCTCTACAGCTTCACACTTATCGCTAATGGCCAGAGCATG
ValLysGlnGlyAspAspPheLysGlyArgProAspLeuTyrSerPheThrLeuIleAlaAsnGlyGlnSerMet 385        395        405        415        425        435        445        455
ACTTTCAACCTGGACCTCTGGACCGCTGGCCTGTGGGCTGCCCGGCCGGGCCAGAATGCGCTGAAGAGTTTCTCC
ThrPheAsnProAspSerGlyProLeuTrpAlaAlaArgArgArgLeuAlaAlaGlnAsnAlaLeuLysSerPheSer 460        470        480        490        500        510        520        530
ATAGCCTCAGACCCAACACTGGCATCCTCTTGCTACTTGGAAGAGCACGTGAGCAAAGAGGCTGAATACTTAATC
IleAlaSerAspProThrLeuAlaSerSerCysTyrLeuGluGluHisValSerLysGluAlaGluTyrLeuIle
```

FIG. 6 (2)

```
            535           545            555            565            575            585            595           605
AGCAAGTTCCAGAAGCTGATGGCAGAGGTTGGCCACTTCGACCCTTTCAAGTATTTGGTGGTGTCAGTGGCCAAT
SerLysPheGlnLysLeuMetAlaGluValGlyHisPheAspProPheLysTyrLeuValValSerValAlaAsn 610           620            630            640            650            660            670           680
GTCATCTGTGCCATATGCTTTGGCAGACGTTATGACCACGATGACCAAGAGCTGCTCAGCATAGTCAATCTAAGC
ValIleCysAlaIleCysPheGlyArgArgTyrAspHisAspAspGlnGluLeuLeuSerIleValAsnLeuSer 685           695            705            715            725            735            745           755
AATGAGTTTGGGGAGGTTACTGGTTCTGGATACCCAGCTGACTTCATTCCTATCCTCCGTTACCTCCCTAACTCT
AsnGluPheGlyGluValThrGlySerGlyTyrProAlaAspPheIleProIleLeuArgTyrLeuProAsnSer 760           770            780            790            800            810            820           830
TCCCTGGATGCCTTCAAGGACTTGAATAAGAAGTTCTACAGTTTCATGAAGAAGCTAATCAAAGAGCACTACAGG
SerLeuAspAlaPheLysAspLeuAsnLysLysPheTyrSerPheMetLysLysLeuIleLysGluHisTyrArg 835           845            855            865            875            885            895           905
ACATTTGAGAAGGGCCACATCCGGGACATTGTCAGGACATTGTCAGGACCCTCAGAGCCTCAGAGGACGAGGAGGCTGGACGAG
ThrPheGluLysGlyHisIleArgAspIleThrAspSerLeuIleGluHisCysGlnAspArgArgLeuAspGlu 910           920            930            940            950            960            970           980
AATGCCAATGTCCAGCTCCTCAGATGATAAGGTCATTACGATTGTTTTTGAGGTTGAGCTGGGTTTGACACA
AsnAlaAsnValGlnLeuSerAspAspLysValIleThrIleValPheAspLeuPheGlyAlaGlyPheAspThr 985           995            1005           1015           1025           1035           1045          1055
ATCACAACTGCTATCTCTTTGAGCCTCATGTACCTGGTAACCAACCCTAGGATACAGAGAAAGATCCAGGAGGAG
IleThrThrAlaIleSerTrpSerLeuMetTyrLeuValThrAsnProArgIleGlnArgLysIleGlnGluGlu
```

FIG. 6 (3)

```
              1060       1070       1080       1090       1100       1110       1120       1130
TTAGACACAGTGATTGGCAGGGATCGGCAGCCCCGGCTTTCTGACAGCCTCAGCTGCCCTATCTGGAGGCCTTC
LeuAspThrValIleGlyArgAspArgGlnProArgLeuSerAspArgProGlnLeuProTyrLeuGluAlaPhe 1135       1145       1155       1165       1175       1185       1195       1205
ATCCTGGAGACCTTCCGACATTCATCCTTTGTCCCATTCACCATCCCCACAGCACCATAAGAGATACAAGTCTG
IleLeuGluThrPheArgHisSerSerPheValProPheThrIleProHisSerThrIleArgAspThrSerLeu 1210       1220       1230       1240       1250       1260       1270       1280
AATGGCTTCTATATCCCCAAGGGACACTGTGTCTCTTTGTGAACCAGTGGCAGGTTAACCATGACCAGGAACTATGG
AsnGlyPheTyrIleProLysGlyHisCysValPheValAsnGlnTrpGlnValAsnHisAspGlnGluLeuTrp 1285       1295       1305       1315       1325       1335       1345       1355
GGTGATCCAAAACGAGTTCCGGCCCTGAAAGGTTTCTTACCTCCAGTGGCACTCTGGACAAACACCTGAGTGAGAAG
GlyAspProAsnGluPheArgProGluArgPheLeuThrSerSerGlyThrLeuAspLysHisLeuSerGluLys 1360       1370       1380       1390       1400       1410       1420       1430
GTCATTCTCTCTTTGGTTTGGGCAAGGCGAAAGTGCATTGGGGAGACCATTGGCCGACTGGAGGTTCTTTCTTCCTG
ValIleLeuPheGlyLeuGlyLysArgLysCysIleGlyGluThrIleGlyArgLeuValPheLeuPheLeu 1435       1445       1455       1465       1475       1485       1495       1505
GCCATCTTGCTGCAGCAAATGGAATTTAATGTGTCACCAGGCGAGAAGGTGGATATGACTCCTGCCTATGGCTG
AlaIleLeuLeuGlnMetGluPheAsnValSerProGlyGluLysValAspMetThrProAlaTyrGlyLeu 1510       1520       1530       1540       1550       1560       1570       1580
ACTTTAAAACATGCCCGCTGTGAGCACTTCCAAGTGCAGATGCGGTTCCTTCTGGTCCTTGAGCAGCAGCCGAT
ThrLeuLysHisAlaArgCysGluHisPheGlnValGlnMetArgSerSerGlyProArgAlaAlaAlaAlaAsp
```

FIG. 6(4)

```
        1585       1595       1605       1615       1625       1635       1645       1655
CGACCAGCAGCCGACCGATCGAGCAGCCATGATCGAGCCATGATCCAAACAACGGCCCCACCCGTCAAACAG
ArgAlaAlaAlaAlaAspArgAlaAlaAlaAlaAspArgAlaMetIleGlnThrThrAlaProProValLysGlu 1660       1670       1680       1690       1700       1710       1720       1730
AGCAGCTTCGTGGAAAAGATGAAGAAAACGGGAAGGAACATTATCGTATTCTATGGCTCCCAGACGGGAACCGCT
SerSerPheValGluLysMetLysLysThrGlyArgAsnIleIleValPheTyrGlySerGlnThrGlyThrAla 1735       1745       1755       1765       1775       1785       1795       1805
GAGGAGTTTGCCAACCGGCTGTCCAAGGATGCCCACCGGCTACGGGATGCGGGGCATGTCCGCAGACCCTGAAGAG
GluGluPheAlaAsnArgLeuSerLysAspAlaHisArgTyrGlyMetSerAlaArgGlyMetSerAlaAspProGluGlu 1810       1820       1830       1840       1850       1860       1870       1880
TATGACTTGGCCGACCTGAGCAGCCTGCCTGAGATCGAGAAGTCCCTGGTAGTCTTCTGCATGGCCACATACGGA
TyrAspLeuAlaAspLeuSerSerLeuProGluIleGluLysSerLeuValValPheCysMetAlaThrTyrGly 1885       1895       1905       1915       1925       1935       1945       1955
GAGGGGGACCCCACGGACAATGCGGCAGGACTTCTATGACTGGCTGCAGGAGACTGACGTGGACCTCACTGGGTC
GluGlyAspProThrAspAsnAlaGlnAspPheTyrAspTrpLeuGlnGluThrAspValAspLeuThrGlyVal 1960       1970       1980       1990       2000       2010       2020       2030
AAGTTTGCTGTATTGTTCTTGGGAACAAGACCTATGAGCACTTCAATGCCATGGGCAAGTATGTGGACCAGCGG
LysPheAlaValPheGlyLeuGlyAsnLysThrTyrGluHisPheAsnAlaMetGlyLysTyrValAspGlnArg 2035       2045       2055       2065       2075       2085       2095       2105
CTGGAGCAGCTTGCCCCCAGCCATCTTTGAGTTGGGCCTTGATGATGACGGAACTTGAAGAGGATTTC
LeuGluGlnLeuAlaGlnArgIlePheGluLeuGlyLeuAspAspGlyAsnLeuGlyLeuGluAspPhe
```

FIG. 6 (5)

```
         2110      2120      2130      2140      2150      2160      2170      2180
ATCACGTGGAGGGAGCAGTTCTGCGCCAGCTGTGTGCCGAGTTCTTTGGGTAGAAGCCACTGGGAGGAGTCGAGC
IleThrTrpArgGluGlnPheTrpProAlaValCysGluPhePheGlyValGluAlaThrGlyGluGluSerSer 2185      2195      2205      2215      2225      2235      2245      2255
ATTCCCAGTACTATGAGCTCGTGGTCCACGAAGACATGGACGTAGCAAGGTGTACACGGGTGAGATGGGCCGTCTG
IleArgGlnTyrGluLeuValValHisGluAspMetAspValAlaLysValTyrThrGlyGluMetGlyArgLeu 2260      2270      2280      2290      2300      2310      2320      2330
AAGAGCTACGAGAACCAGAAACCCCCTTCGATGCTAAGAATCCATTCCTGGCTGCTGTCACCGCCAACCGGAAG
LysSerTyrGluAsnGlnLysProProPheAspAlaLysAsnProPheLeuAlaAlaValThrAlaAsnArgLys 2335      2345      2355      2365      2375      2385      2395      2405
CTGAACCAAGGCCACTGAGCGGCATCGAGGTTGGACATCTCAGACTCCAAGATCAGGTATGAATCT
LeuAsnGlnGlyThrGluArgHisLeuMetHisLeuGluLeuAspIleSerAspSerLysIleArgTyrGluSer 2410      2420      2430      2440      2450      2460      2470      2480
GGAGATCACGTGGCTGTGTACCCAGCCAATGACTCAGCCAACCAGATTGGGGAGATCCTGGGAGCTGAC
GlyAspHisValAlaValTyrProAlaAsnAspSerAlaAsnGlnIleGlyGluIleLeuGlyAlaAsp 2485      2495      2505      2515      2525      2535      2545      2555
CTGGATGTCATCATGTCTCTAAACAATCTCGATGAGGAGTCAAACAAGAAGCATCCGTTCCCTGCCCCACCACC
LeuAspValIleMetSerLeuAsnAsnLeuAspGluGluSerAsnLysLysHisProPheProCysProThrThr 2560      2570      2580      2590      2600      2610      2620      2630
TACCGCACGGCCCTCACCTACTACCTGGACATCACTAACCCGCCACGACCAATGTGCTCTACGAACTGGCACAG
TyrArgThrAlaLeuThrTyrTyrLeuAspIleThrAsnProProArgThrAsnValLeuTyrGluLeuAlaGln
```

FIG. 6 (6)

```
       2635       2645       2655       2665       2675       2685       2695       2705
TACGCCCTCAGAGCCCTCGGAGCAGGAGCCACCTGCACAAGATGGCTCATCCTCAGGCGAGGCAAGGAGCTGTAC
TyrAlaSerGluProSerGluGlnHisLeuHisLysMetAlaSerSerGlyGluGlyLysGluLeuTyr 2710       2720       2730       2740       2750       2760       2770       2780
CTGAGCTGGTGGTGGAAGCCGGAGCCCCGGAAGGCCACATCCTCCAAGACTACCATCACTGGGCGCCACCCATC
LeuSerTrpValValGluAlaArgArgHisIleLeuAlaIleLeuGlnAspTyrProSerLeuArgProProIle 2785       2795       2805       2815       2825       2835       2845       2855
GACCACCTGTGTGAGCTGCTGCCACGCCTGCAGGCCCGATACTACTCCATTGCCTCATCCTCCAAGTCCACCCC
AspHisLeuCysGluLeuLeuProArgLeuGlnAlaArgTyrTyrSerIleAlaSerSerLysValHisPro 2860       2870       2880       2890       2900       2910       2920       2930
AACTCCGTGCACATCTGTGCCGTGGCCGTGGAGTACGAAGGCGAAGTCTGGCCCAGTGAACAAGGGGTGGCCACT
AsnSerValHisIleCysAlaValAlaValAlaValGluTyrGluAlaLysSerGlyArgValAsnLysGlyValAlaThr 2935       2945       2955       2965       2975       2985       2995       3005
AGCTGGCTTCGGGCCAAGGAACCAGGCGAGAATGGCGGCCCCCTGGTACCCATGTTCGTGCCCAAATCT
SerTrpLeuArgAlaLysGluProGlyAlaGlyGlyArgAlaLeuValProMetPheValArgLysSer 3010       3020       3030       3040       3050       3060       3070       3080
CAGTTCCGGCTTGCCTTTCAAGTCCACCACCTGTCATCATGGTGGGCCCCGGCACTGGGATTGCCCCTTTCATG
GlnPheArgLeuProPheLysPheSerThrThrProValIleMetValGlyProGlyThrGlyIleAlaProPheMet 3085       3095       3105       3115       3125       3135       3145       3155
GGCTTCATCCAGGAACGAGCTTGGCTTCGAGAGCAAGGAGGTGGGAGAGACGCTGCTATACTATGGCTGC
GlyPheIleGlnGluArgAlaTrpLeuArgGluArgGluValGlyGluThrLeuLeuTyrTyrGlyCys
```

FIG. 6 (7)

```
       3160      3170      3180      3190      3200      3210      3220      3230
CGGCGCTCGGATGAGGACTATCTGTACCGTGAAGAGCTAGCCCGCTTCCACAAGGACGGTGCCCTCACGCAGCTT
ArgArgSerAspGluAspTyrLeuTyrArgGluGluLeuAlaArgPheHisLysAspGlyAlaLeuThrGlnLeu 3235      3245      3255      3265      3275      3285      3295      3305
AATGTGGCCTTTTCCCGGAGCAGGGAGCCCACAAGGTCTATGTCCAGCACCTTCTGAAGAGACAGGGAACACCTG
AsnValAlaPheSerArgGluArgGluGlnAlaHisLysValTyrValGlnHisLeuLeuLysArgAspArgGluHisLeu 3310      3320      3330      3340      3350      3360      3370      3380
TGGAAGCTGATCCACGAGGGCCGGTGCCCACATCTATGTGTGCGGGGATGCTGCTGAAATATGGCCAAAGATGTGCAA
TrpLysLeuIleHisGluGlyGlyAlaHisIleTyrValCysGlyAspAlaAlaArgAsnMetAlaLysAspValGln 3385      3395      3405      3415      3425      3435      3445      3455
AACACATTCTATGACATTGTGGCTGAAGTTCGGGCCCATGGAGCACACCCAGGCTGTGGACTATGTTAAGAAGCTG
AsnThrPheTyrAspIleValAlaGluPheGlyProMetGluHisThrGlnAlaValAspTyrValLysLysLeu 3460      3470      3480      3490
ATGACCAAGGGGCCGCTACTCACTAGATGTGTGGAGCTAG
MetThrLysGlyArgTyrSerLeuAspValTrpSer***
```

FIG. 7 (1)

```
         10         20         30         40         50         60         70         80
ATGATCCAAACAACGGCCCCACCCGTCAAAGAGACAGCTTCCTGGAAAAGATGAAGAAAACGGGAAGAACATT
MetIleGlnThrThrAlaProProValLysGluSerSerPheValGluLysMetLysLysThrGlyArgAsnIle 85         95        105        115        125        135        145        155
ATCGTATTCTATGGCCTCCCAGAGACGGGAACCGGCTGAGGAGTTTGCCAACCGGCTGTCCAAGGATGCCACCGCTAC
IleValPheTyrGlyLeuProGluThrGlyThrGlyThrAlaGluPheAlaAsnArgLeuSerLysAspAlaHisArgTyr 160        170        180        190        200        210        220        230
GGGATGCGGGGCATGTCCGCAGACCCTGAAGAGTATGACTGGCCGACTGGCCTGAGCAGCCTGCCTGAGATCGACAAG
GlyMetArgGlyMetSerAlaAspProGluGluTyrAspLeuAlaAspLeuSerSerLeuProGluIleAspLys 235        245        255        265        275        285        295        305
TCCCTGGTAGTCTTCTGCATGGCCACATGGCGGAGAGGGCACCCGGACAATGGCCAGGACTTCTATGACTGG
SerLeuValValPheCysMetAlaThrTyrGlyGluGlyAspProThrAspAsnAlaGlnAspPheTyrAspTrp 310        320        330        340        350        360        370        380
CTGCAGGAGACTGACGTGGACCTCACTGGGGTCAAGTTTGCTGTATTTGGCTCTTGGGAACAAGACCTATGAGCAC
LeuGlnGluThrAspValAspLeuThrGlyValLysPheAlaValPheGlyLeuGlyAsnLysThrTyrGluHis 385        395        405        415        425        435        445        455
TTCAATGCCATGGGCAAGTATGTGGACGGCTTGGCGCCCCAGCCCATCTTTGAGTTGGGCCTT
PheAsnAlaMetGlyLysTyrValAspGlyLeuArgLeuGlnLeuGlyAlaGlnArgIlePheGluLeuGlyLeu 460        470        480        490        500        510        520        530
GGTGATGATGACGGGAACTTCATCACGTGGAGGAGCAGTTCTGCCAGCTGTGTGCCGAGTTC
GlyAspAspAspGlyAsnLeuGluGluAspPheIleThrTrpArgGluGlnPheTrpProAlaValCysGluPhe
```

FIG. 7 (2)

```
         535            545            555            565            575            585            595             605
TTTGGGTAGAAGCCACTGGGAGGAGGAGTCGAGCATTCGCCAGTATGAGCTCGTGCTGGTCCACGAAGACATGGACGTA
PheGlyValGluAlaThrGlyGlyGlyValGluSerSerIleArgGlnTyrGluLeuValHisGluAspMetAspVal 610            620            630            640            650            660            670             680
GCCAAGGTGTACACGGGTGAGATGGGCCGTCTGAAGAGCTACGAGAACCAGAAACCCCCTTCGATGCTAAGAAT
AlaLysValTyrThrGlyGluMetGlyArgLeuLysSerTyrGluAsnGlnLysProProPheAspAlaLysAsn 685            695            705            715            725            735            745             755
CCATTCCTGGCTCCTGTCACCGCCAACCGGAAGCTGAACAATGACTGAGCGGCATCTAATGCACCTGGAGTTG
ProPheLeuAlaAlaValThrAlaAsnArgLysLeuAsnAsnGlnGlyThrGluArgHisLeuMetHisLeuGluLeu 760            770            780            790            800            810            820             830
GACATCTCAGACTCCAAGATCAGGTATGAGAATCTGGAGTACCGTGGCTGTGTACCCAGCCAATGACTCAGCCCTG
AspIleSerAspSerLysIleArgTyrGluSerGlyAspHisValAlaValTyrProAlaAsnAspSerAlaLeu 835            845            855            865            875            885            895             905
GTCAACCAGATTGGGGAGATCCTGGGAGCTCGACCTGCACTCATGTCTCTAAACAATCTCGATGAGGAGTCA
ValAsnGlnIleGlyGluIleLeuGlyAlaAlaAspLeuAspValIleMetSerLeuAsnAsnLeuAspGluGluSer 910            920            930            940            950            960            970             980
AACAAGAAGCATCCGTTCCCCTGCCCCACCACCTACCGGACCGCACTGGACATCACTACTACTAACCCG
AsnLysLysHisProPheProCysProProThrThrTyrArgThrAlaLeuThrTyrLeuAspIleThrAsnPro 985            995            1005           1015           1025           1035           1045            1055
CCACCGCCAATGTGCTTACGAACTGGACACGTAGCCCCTCAGAGCCGGAGCAGGACCACCTGCAACAAGATG
ProArgThrAsnValLeuTyrGluAlaGlnTyrAlaSerGluProSerGluGlnGluHisLeuHisLysMet
```

FIG. 7 (3)

```
              1060            1070            1080            1090            1100            1110            1120            1130
GCCTCATCCTCAGGCGAGGGCAGGGCAAGGAGCTGTACCTGAGCTGGTGGTTGGAAGCCCGGAGGCACATCCTAGCCATC
AlaSerSerGlyGluGluGlyLysGluLeuTyrLeuSerTrpValValGluAlaArgArgHisIleLeuAlaIle 1135            1145            1155            1165            1175            1185            1195            1205
CTCCAAGACTACCCATCACTGGGCCCCACCCATGACCACCTGTGTGAGCTGTCCGCACGCCTGCCACGCCTGCCCGATAC
LeuGlnAspTyrProSerLeuArgProProIleAspHisLeuCysGluLeuLeuProArgLeuGlnAlaArgTyr 1210            1220            1230            1240            1250            1260            1270            1280
TACTCCATTGCCTCATCCTCCAAGGTCCACCCCAACTCCGTGCACATCTGTGCCGTGGAGTACGAAGCG
TyrSerIleAlaSerSerLysValHisIleProAsnSerValHisIleCysAlaValAlaValGluTyrGluAla 1285            1295            1305            1315            1325            1335            1345            1355
AAGTCTGGCCGAGTGAACAAGGGGGTGGCCACTAGCTGGCTTCGGGCCAAGGAACCAGCAGGCGAGAATGGCGGC
LysSerGlyArgValAsnLysGlyValAlaThrSerTrpLeuArgAlaLysGluProAlaGlyGluAsnGlyGly 1360            1370            1380            1390            1400            1410            1420            1430
CGGCGCCCTGGTACCCATGTTCCTGCCCAAATCTCAGTTCCGCTTCAAGTCCACCACCACCTGTCATCATG
ArgAlaLeuValProMetPheValArgLysSerGlnPheArgLeuProPheLysSerThrThrProValIleMet 1435            1445            1455            1465            1475            1485            1495            1505
GTGGGCCCCCGGCACTGGGATTGCCCCTTTCATGGGCTTCATCCAGGAACGAGCTTGGCTTCGAGAGCAAGGCAAG
ValGlyProGlyThrGlyIleAlaProPheMetGlyPheIleGlnGluArgAlaTrpLeuArgGluGlnGlyLys 1510            1520            1530            1540            1550            1560            1570            1580
GAGGTGGGAGAGACGCTGCTATACTACTGGCTGCCGGCCTCGAGGACTATCTGTAAGAGACTAGCC
GluValGlyGluThrLeuLeuTyrTyrGlyCysArgArgSerAspGluAspTyrLeuTyrArgGluLeuAla
```

FIG. 7 (4)

```
         1585       1595       1605       1615       1625       1635       1645       1655
CGCTTCCACAAGGACGGTGCCCTCACGGCAGCTTAATGTGGCCCTTTCCCGGGAGCAGGCCCACAAGGTCTATGTC
ArgPheHisLysAspGlyAlaLeuThrGlnLeuAsnValAlaPheSerArgGluGlnAlaHisLysValTyrVal 1660       1670       1680       1690       1700       1710       1720       1730
CAGCACCTTCTGAAGAGAGACAGGGAACACCTGTGGAAGCTGATCCACGAGGGCCGTGCCACAGAGGGCCACATCTATGTGTGC
GlnHisLeuLeuLysArgAspArgGluHisLeuTrpLysLeuIleHisGluGlyGlyAlaHisIleTyrValCys 1735       1745       1755       1765       1775       1785       1795       1805
GGGGATGCTCGAAATATGGCCAAAAGATGTGCAAAAACACATTCTATGACAATTCTGGCTGAGTTCGGGCCCATGGAG
GlyAspAlaArgAsnMetAlaLysAspValGlnAsnThrPheTyrAspIleValAlaGluPheGlyProMetGlu 1810       1820       1830       1840       1850       1860       1870
CACACCCAGGCTGTGGACTATGTTAAGAAGCTGATGACCAAGGGCCGCTACTCACTAGATGTGTGGAGCTAG
HisThrGlnAlaValAspTyrValLysLysLeuMetThrLysGlyArgTyrSerLeuAspValTrpSer***
```

CHIMERIC FUSED MONOOXYGENASE OF CYTOCHROME P-450 AND NADPH-CYTOCHROME P-450 REDUCTASE

This is a continuation of copending application Ser. No. 07/081,647 filed on Aug. 4, 1987, now abandoned.

BACKGROUND OF THE INVENTION

The present invention relates to a novel monooxygenase having, in the same molecule, a monooxygenase activity and a reducing power supplying ability from NADPH required for said monooxygenase activity; genes which code for said monooxygenase; yeast expression plasmids containing said genes; and yeast strains transformed with said expression plasmids.

More particularly, it relates to monooxygenase having, in the same molecule, a monooxygenase activity derived from cytochrome P-450 (hereinafter referred to as "P-450") and reducing power supplying ability from NADPH derived from NADPH-cytochrome P-450 reductase (hereinafter referred to as "reductase"); chimeric fused enzyme genes which code for said monooxygenase; yeast expression plasmids containing said genes; and yeast strains transformed with said expression plasmids and to a process for producing said monooxygenase by cultivating said transformed yeast strains.

P-450 is a heme protein existing widely in biological fields from microorganisms to mammals and catalyzes monooxygenase activity toward a wide variety of lipophilic compounds as substrates. Such a wide variety of substrate specificity exhibited by P-450 are attributable to molecular diversity of P-450. That is, there are many molecular forms of P-450 whose substrate specificity is wide and overlapping each other. Many of them are common in electron transfer routes. In case of liver microsome, only one form of reductase containing flavin adenin mononucleotide and flavin mononucleotide as coenzymes mainly supplies electrons from NADPH to substrate-bounded P-450. Therefore, P-450 exhibits monooxygenase activity only when it binds a substrate and couples with reductase.

We have already succeeded in production of enzyme proteins which show monooxygenase activity by isolating P-450MC and reductase genes present in rat liver and expressing these genes in yeasts as their hosts P-450 MC is a gene coding for rat liver cytochrome P-450 inducible by 3-methylcholanthrene (MC refers to 3-methylcholanthrene) [Oeda et al., DNA Vol. 4 No. 3 p203-210 (1985); Murakami et al., DNA Vol. 5 No. 1 p. 1-10 (1986)]. P-450 MC synthesized in yeasts constituted electron-transport chains in yeast microsome by coupling with yeast reductase and exhibited monooxygenase activity inherent to rat P-450MC. The P-450MC-producing yeast strains were able to convert acetanilide to acetaminophene useful as a medicine.

Therefore, P-450MC-producing yeast strains or P-450MC obtained from transformed yeasts can be applied to oxidative reaction process of useful substances and further to oxidative removal of harmful substances from industrial waste.

We have made researches in an attempt to enhance monooxygenase activity of P-450MC and produced yeast strain which produces P-450MC and reductase simultaneously [Murakami et al, DNA Vol. 5 No. 1 p. 1-10 (1986)].

SUMMARY OF THE INVENTION

Now, the inventors have further developed the researches and connected both genes for P-450 and reductase into single gene, whereby chimeric fused enzyme gene is constructed which codes for monooxygenase having in the same molecule the monooxygenase activity of cytochrome P-450 and the reducing power supplying ability from NADPH which is derived from NADPH-cytochrome P-450 reductase and this gene is introduced into yeast expression vector to construct an expression plasmid.

BRIEF DESCRIPTION OF DRAWINGS

FIG. 2 shows DNA sequence, in plasmid pAMP19 of the present invention, of a region which codes for P-450/reductase chimeric fused monooxygenase and amino acid sequence thereof.

FIG. 3 shows DNA sequence, in plasmid pALP1 of the present invention, of a region which codes for P-450/reductase chimeric fused monooxygenase and amino acid sequence thereof.

FIG. 4 shows DNA sequence, in plasmid pALP17 of the present invention, of a region which codes for P-450/reductase chimeric fused monooxygenase and amino acid sequence thereof.

FIG. 5 shows DNA sequence, in plasmid pALP25 of the present invention, of a region which codes for P-450/reductase chimeric fused monooxygenase and amino acid sequence thereof.

FIG. 6 shows DNA sequence, in plasmid pALP4 of the present invention, of a region which codes for P-450/reductase chimeric fused monooxygenase and amino acid sequence thereof.

FIG. 7 shows DNA sequence, in plasmid pAXP2 of the present invention, of a region which codes for soluble reductase and amino acid sequence thereof.

Figure 1:
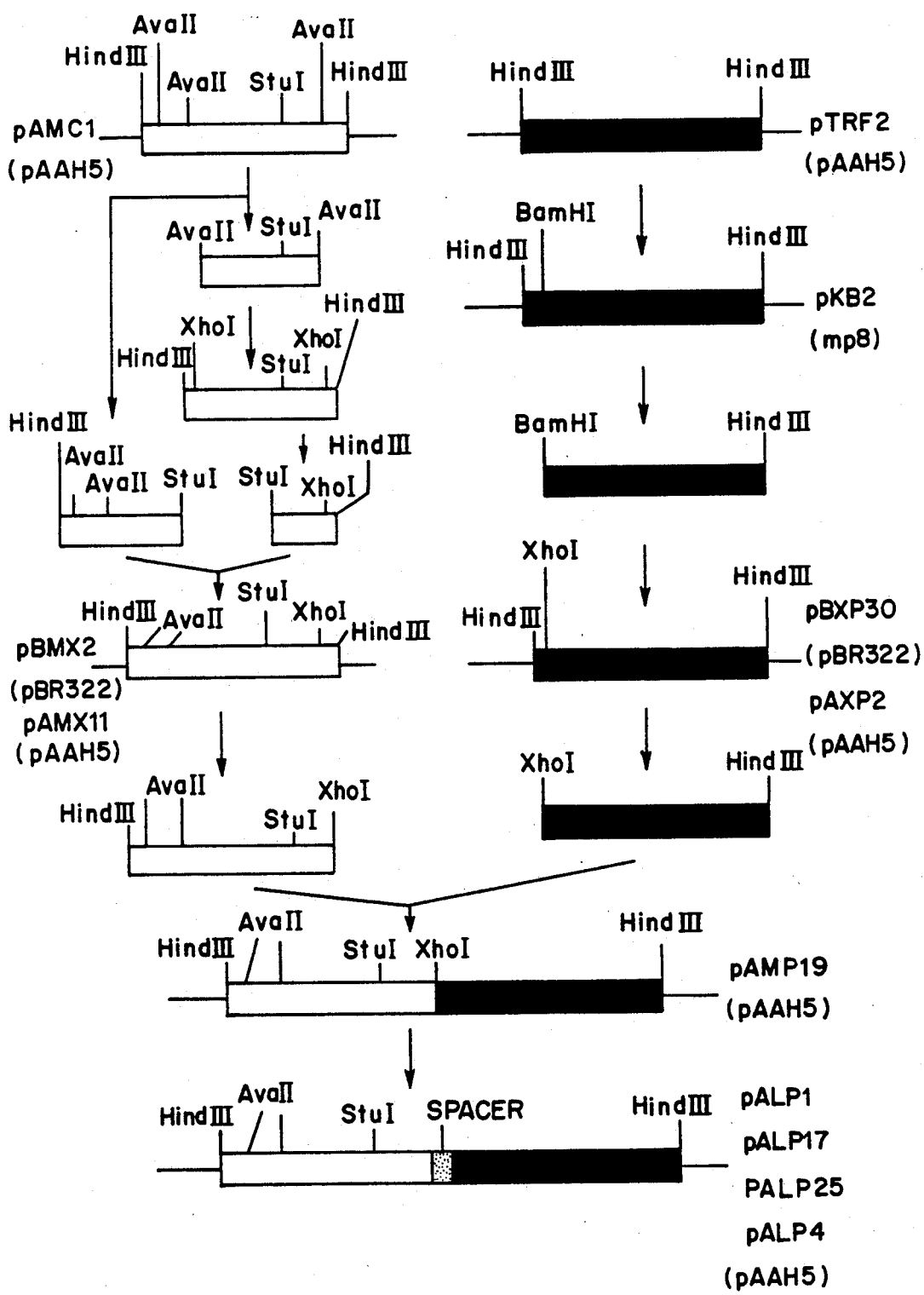
FIG. 1 shows diagrams of the constructions of plasmids pAMP19, pALP1, pALP17, pALP25 and pALP4 of the present invention.

The yeast strains in which said expression plasmid is introduced produce a chimeric fused enzyme of P-450 and reductase and exhibit monooxygenase activity. Oxidation activity thereof is higher than that of yeast strains in which P-450 is singly produced and it has been found that it is highly useful for oxidative reaction process. Further, single molecule of thus obtained chimeric fused enzyme possesses both functions of electron transportation and oxidation of substrate. Thus, this enzyme is a novel enzyme having excellent properties.

The chimeric fused gene of the present invention can be constructed by connecting the region necessary for exhibition of function of NADPH-cytochrome P-450 reductase to the region necessary for monooxygenase activity of P-450 gene.

Typical examples of P-450 gene and reductase gene are rat liver P-450 gene and reductase gene, but it is also possible to use P-450 and reductase genes of other living origins.

The P-450 genes and reductase genes can be produced by conventional methods employed in the technical field of the present invention. For example, with reference to rat liver P-450 gene, this gene can be taken out from known plasmid pAMC1 containing it [Oeda et al., DNA Vol. 4 No. 3, p. 203-210 (1985)].

Similarly, rat reductase gene can be taken out from plasmid pTRF2 containing this gene [Murakami et al., DNA Vol.5 No. 1 p. 1-10 (1986)] by a conventional process.

The expression plasmid which expresses chimeric fused enzyme gene of the present invention can be constructed by inserting the chimeric gene constructed as above into a suitable plasmid by a conventional process.

As the expression plasmids, there may be used known expression vectors, for example, those containing yeast alcohol dehydrogenase I (ADH1) promoter, PGK promoter, G3PDH promoter, GAL10 promoter, etc., yeast expression vector pAAH5 containing yeast ADH1 gene promoter and terminator (This is available from Washington Research Fundation and can be produced by the method disclosed in Ammerer et al, Methods in Enzymology, 101 part C p192-201 and promoter of yeast ADH1 gene is included in U.S. patent application Ser. No. 299,733 of Washington Research Fundation and the patentee's grant of license is necessary for commercial working in U.S.A.), pJDB219, etc. There are no limitations as far as they have promoters and terminators which efficiently function in host cells. Furthermore, structures of expression plasmids have no limitations and there may be used any of those which are stably held in yeasts.

For expression of the chimeric enzyme gene of the present invention, yeasts, for example, *Saccharomyces cerevisiae* strain AH22, *Saccharomyces cerevisiae* strain SHY3, *Saccharomyces cerevisiae* strain NA87-11A, etc. can be conveniently used as hosts. Transformation of these hosts by expression plasmids containing chimeric fused enzyme gene of this invention can be carried out by the known methods such as the protoplast method, and the alkaline metal (LiCl) method, etc.

The chimeric fused enzyme of the present invention can be produced by cultivation of thus obtained transformed microorganisms.

Cultivation of the transformed microorganisms obtained by the present invention can be performed by the common culturing methods.

Thus obtained chimeric enzymes can be extracted and purified from cells after cultivation by conventional methods employed in the field of the present invention. Microsomal fraction is prepared by, for example, treating the cells with Zymolyase to prepare spheroplasts and destructing them by sonication or by mechanical methods using French press, glass beads, etc. This microsomal fraction can be applied to DEAE-cellulose and 2',5'-ADP Sepharose 4B column chromatography to purify the fused enzyme.

The following examples are given to illustrate the present invention in more detail. The present invention is not limited thereto, but usual or obvious modification or alteration of the disclosed embodiments are possible.

EXAMPLE 1

Construction of Plasmid pAMP19

Outline of construction of plasmid pAMP19 is shown in FIG. 1.

Step 1: Construction of Plasmid pBMX2

About 10 μg of P-450MC expression plasmid pAMC1 (disclosed in Japanese Patent KOKAI (Laid-Open) Nos. 88878/86 and 56072/86 and U.S. patent application Ser. No. 741,592) was subjected to digestion reaction at 37° C. for 2 hours in 50 μl of a restriction enzyme buffer solution M [10 mM Tris-HCl (pH 7.5), 10 mM MgCl$_2$, 50 mM NaCl and 1 mM dithiothreitol] by addition of 20 units of restriction enzyme Hind III (purchased from Takara Shuzo Co., Ltd.). The reaction mixture was electrophoresed on 0.8% low melting point agarose gel. Then, a gel band containing about 1.8 kb DNA fragment corresponding to coding region of P-450MC was cut out and was heated at 65° C. for 5 minutes to melt the gel. To the molten gel was added 2 volumes of TE buffer solution [10 mM Tris-HCl (pH 8.0) and 0.5 mM EDTA] and to the mixture was added an equal volume of phenol saturated with TE buffer solution, followed by stirring and centrifuging. Then, aqueous layer was isolated and 2 volumes of chilled ethanol was added thereto to effect precipitation with ethanol to recover DNA fragment. About 3 μg of this Hind III fragment of about 1.8 kb was dissolved in a restriction enzyme buffer solution M and 10 units of restriction enzyme Ava II was added thereto, followed by incubation at 37° C. for 1 hour. Reaction mixture was electrophoresed on low melting point agarose gel and in the similar manner, Ava II fragment of about 1.2 kb was recovered. To this fragment was added about 0.5 μg of the following synthesized DNA linker 5'-terminal of which was previously phosphorylated.

(having recognition sites of Ava II and Hind III at both the terminals, respectively and having xho I site, and synthesized by 380 A type DNA synthesize manufactured by Applied Biosystem Inc.). The Ava II fragment and DNA linker were incubated overnight at 15° C. with 300 units of T4 DNA ligase (Takara Shuzo Co., Ltd.) in 20 μl of DNA ligase buffer solution [67 mM Tris-HCl (pH 7.6), 6.7 mM MgCl$_2$, 10 mM dithiothreitol and 0.5 mM ATP]. Then, this was digested simultaneously with restriction enzymes Stu I (Takara Shuzo Co., Ltd.) and Hind III and electrophoresed on low melting point agarose gel to recover about 450 bp Stu I-Hind III fragment. On the other hand, about 2 μg of Hind III fragment of about 1.8 kb prepared from plasmid pAMC1 was digested with about 10 units of restriction enzyme Stu I and in the same manner as above, DNA fragment of about 1.2 kb was recovered.

Thus obtained Hind III-Stu I fragment of about 1.2 kb and Stu I-Hind III fragment of about 450 bp were cloned to Hind III site of plasmid pBR322. That is, about 500 ng of Hind III-Stu I fragment of about 1.2 kb, about 100 ng of Stu I-Hind III fragment of about 450 bp and about 1 μg of pBR322 previously digested with Hind III and subjected to an alkaline phosphatase treatment were incubated overnight at 15° C. with addition of 300 units of T4 DNA ligase in 20 μl of DNA ligase buffer solution. By using the reaction mixture, *Escherichia coli* strain DHI (ATCC 33849) was transformed and ampicillin-resistant colonies were selected. From the colonies, plasmid DNA was prepared according to the method of Birnboim-Doly and digested with Hind III and Stu I to confirm the DNA structure. Thus obtained plasmid was named pBMX2.

Step 2: Construction of Plasmid pKB2

Rat liver reductase is released from microsome membrane with protease to become a solube protein. Amino acid sequence of the site (mark ↓) cleaved by digestion with protease and the corresponding base sequence are:

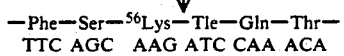

—Phe—Ser—⁵⁶Lys—Ile—Gln—Thr—
TTC AGC AAG ATC CAA ACA

By changing codon AAG for Lys residue to AGG, $^{56}$Lys residue is converted to Arg residue and simultaneously BamH I recognition site (-GGATCC-) is newly produced. Therefore, by utilizing this BamH I site, genes which code for soluble reductase protein can be easily isolated.

About 5 μg of reductase expression plasmid pTRF2 [Murakami et al., DNA Vol. 5 No. 1 p. 1–10 (1986)] was digested with restriction enzyme Hind III and DNA fragment of about 2.3 kb corresponding to coding region of reductase was recovered from low melting point agarose gel. About 1 μg of thus obtained DNA fragment together with about 100 ng of M13 phage vector mp8 RF DNA previously digested with Hind III were incubated overnight at 15° C. with addition of 300 units of T4 DNA ligase in 20 μl of DNA ligase buffer solution. By using the reaction mixture, E. coli strain JM103 was transformed. Plaques which become transparent in the presence of 2 mM IPTG (isopropyl-β-D-thiogalactopyranoside) and 0.2% X-gal (5-bromo-4-chloro-3-indoyl-β-D-galactoside) were selected and phage ss-DNA and RF DNA were prepared from culture sup and the cell lysate, respectively, of the plaque-infected JM 103 cells. The RF DNA was digested with Hind III to confirm the DNA structure. About 2 μg of ss-DNA was heated to 65° C. for 1 hour together with about 100 ng of synthesized DNA primer (5'GTTTGGATCCTGCTGAACT-3', synthesized by 380 A type DNA synthesizer of Applied System Inc.) and then gradually cooled to anneal them. To this mixture were added 1 μl of 0.2 Tris-HCl, (pH 7.5), 0.1 M MgCl$_2$, 0.1M dithiothreitol, 1 μl of each of 10 mM dATP, dGTP and dTTP, 0.5 μl of 0.1 mM dCTP, 1.5 μl of [$^{32}$P]dCTP (410Ci/mmol, supplied by Amersham), 2 μl of water, 300 units of T4 DNA ligase and 5 units of DNA polymerase I (Klenow enzyme), followed by incubation at room temperature for 1 hour. Then, 1 μl of 10 mM dCTP was added and incubation was continued at 25° C. overnight. After completion of the reaction, 30 μl of water was added to make up 50 μl, followed by adding 50 μl of 1.6 M NaCl/13% polyethylene glycol and leaving it on ice for 15 minutes. The centrifugally recovered precipitate was washed with 100 μl of 0.8M NaCl/6.5% polyethylene glycol and dissolved in 180 μl of TE buffer solution. To the solution was added 20 μl of 2N NaOH and this was left to stand at room temperature for 5 minutes. This was laid on mixtures of 0.9 ml each of discontinuous density gradient consisting of 0.2N NaOH, 1M NaCl, 2 mM EDTA and 5, 10, 17.5 and 20% sucrose and was centrifuged at 37,000 rpm at 4° C. for 2 hours by AH-650 rotor (Sorvall) followed by fractionation to each 0.2 ml of fractions. Radioactivity ($^{32}$P) of each fraction was monitored and ds-DNA fractions fractionated at the bottom of tube were collected. This was neutralized and then E. coli strain JM 103 was retransformed therewith. Plaques were cultured to prepare RF DNA. The RF DNA was digested with various restriction enzymes to confirm the DNA structure. RF DNA containing DNA where BamH I recognition site was produced by changing of condon AAG for $^{56}$Lys residue to AGG was named pKB2.

Step 3: Construction of Plasmid pBXP30

About 5 μg of plasmid pKB2 obtained in step 2 was incubated at 37° C. for 2 hours with addition of 10 units of restriction enzyme Hind III and 10 units of BamH I in 20 μl of restriction enzyme buffer solution M. The reaction mixture was electrophoresed on low melting point agarose gel and BamHI-Hind III fragment of about 2.1 kb was recovered. To about 1 μg of this DNA fragment was added about 100 ng of a synthesized linker:

5'-AGCTTCTCGAGCCAT
AGAGCTCGGTACTAG-5'

(having recognition sites of Hind III and BamH I at both terminals and having Xho I recognition site). This was incubated overnight at 15° C. together with T4 DNA ligase in a DNA ligase buffer solution. Then, this was digested with restriction enzyme Hind III and then subjected to subcloning to Hind III site of pBR322. The objective plasmid having the following structure was named pBXP30.

The plasmid pBXP30 has such a structure that coding region of soluble reductase can be easily taken out by digestion with restriction enzyme Hind III. Furthermore, the translation start codon ATG was located before the cDNA sequence encoding the first amino acid residue Ile of the soluble reductase to produce the soluble reductase by connection of the coding region downstream a suitable promoter. Actually, soluble reductase expression plasmid pAXP2 was constructed by inserting Hind III fragment cut out from pBXP30 into Hind III site of yeast expression vector pAAH5. Yeast S. cerevisiae AH22 strain transformed with this expression plasmid pAXP2 produced soluble reductase in a large amount.

FIG. 7 shows DNA sequence and amino acid sequence of soluble reductase coding region.

Step 4: Construction of Plasmid pAMP19

About 2 μg of plasmid pBMX2 constructed in step 1 and about 2 μg of plasmid pBXP30 constructed in step 3 were respectively incubated at 37° C. for 1 hour with addition of 10 units of restriction enzyme Hind III in 20 μl of restriction enzyme buffer solution M. Then, NaCl was added thereto so that final NaCl concentration in the buffer solution reached 100 mM, followed by addition of 10 units of restriction enzyme Xho I and further incubation for 1 hour at 37° C. The reaction mixture was electrophoresed on a low melting point agarose gel and P-450 coding Hind III-Xho I fragment and reductase coding Xho I-Hind III fragment were recovered, respectively.

About 100 ng of yeast expression vector pAAH5 was digested with restriction enzyme Hind III and subjected to alkaline phosphatase treatment. This was mixed with 200 ng of each of said DNA fragments to carry out DNA ligase reaction. With the resulting reaction mixtures was transformed E. coli strain DH1 and ampicillin-resistant colonies were selected. From the colonies, plasmid DNA was prepared and digested with restriction enzymes Hind III, Xho I, NcoI, etc. to confirm the DNA structure. As shown in FIGS. 1 and 2, plasmid which contains DNA coding for chimeric fused protein, where soluble reductase coding DNA is linked downstream the P-450 gene through a linker was named pAMP19.

EXAMPLE 2

Construction of Plasmid pALP1, pALP17, pALP25, pALP4

Outline of construction of the above plasmids is shown in FIG. 1.

About 2 μg of plasmid pAMP19 constructed in Example 1 was digested with restriction enzyme Hind III and DNA fragment (about 3.5 kb) which codes for the chimeric fused enzyme of P-450 and reductase was recovered and was subcloned to Hind III site of pBR322. This plasmid was named pBMP1. About 1 μg of pBMP1 was digested with restriction enzyme Xho I and thereto was added about 50–100 ng of the following synthetic DNA spacer which had been previously phosphorylated and annealed and T4 DNA ligase reaction was effected.

```
5'-TCGATCGGCTGCTGCTGC
    AGCCGACGACGACGAGCT-5'
```

With the resulting reaction mixture was transformed *E. coli* strain DH1 and from the resulting ampicillin-resistant colonies, plasmid DNA was prepared. Since the synthetic spacer has restriction enzyme Pvu I recognition site, plasmids digested with Pvu I were selected and as shown in FIG. 1 and FIGS. 3, 4, 5 and 6. Plasmids containing chimeric fused protein gene where 1 unit and 3 units of said synthetic spacer were inserted in Xho I site of said synthetic linker in the same direction as above were named pBLP I and pBLP17, respectively. Furthermore, plasmids containing chimeric fused protein gene where 1 unit and 3 units of said synthetic spacer were inserted in Xho I site of said synthetic linker in the direction opposite to the above direction were named pBLP25 and pBLP4, respectively.

In the same manner as in step 4 of Example 1, Hind III fragments of pBLP I, pBLP17, pBLP25, pBLP4 were inserted in Hind III site of expression vector pAAH5 to obtain pALP1, pALP17, pALP25, pALP4. FIGS. 3, 4, 5 and 6 show the DNA sequence and amino acid sequence of chimeric fused enzymes coding regions, in pALP1, pALP17, pALP25 and pALP4, respectively.

EXAMPLE 3

Transformation of Yeast With the Constructed Plasmids

*Saccharomyces cerevisiae* strain AH22 (ATCC 38626) was cultivated in 5 ml of YPD medium (1% yeast extract, 2% polypeptone, 2% glucose) at 30° C. for 18 hours. Thereafter, cells were collected by centrifugation of 1 ml of the culture medium. Thus obtained cells were washed with 1 ml of 0.2M LiCl solution and then suspended in 20 μl of 1M LiCl solution. To the suspension were added 30 μl of 70% polyethylene glycol 4000 solution and 10 μl (about 1 μg) of plasmid pAMP19, pALP1, pALP17, pALP25 or pALP4 and well mixed, followed by incubation at 30° C. for 1 hour. Then, 140 μl of water was added thereto and well mixed. Thereafter, this solution was spread onto SD-synthetic medium plate (2% glucose, 0.67% yeast nitrogen base without amino acids, 20 μg/ml histidine, 2% agar) and incubated at 30° C. for 3 days to obtain transformants AH22 (pAMP19), AH22 (pALP1), AH22 (pALP17), AH22 (pALP25) and AH22 (pALP4) containing plasmids pAMP19, pALP1, pALP17, pALP25 and pALP4, respectively.

EXAMPLE 4

Determination of Expression Amount of Chimeric Fused Protein of P-450 and Reductase P-450MC producing yeast strain AH22 (pAMC1) [Japanese Patent Kokai (Laid-Open) No. 56072/86] and strains AH22 (pAMP19), AH22 (pALP1), AH22 (pALP17), AH22 (pALP25) and AH22 (pALP4) obtained in Example 3 were cultivated in SD-synthetic medium (2% glucose, 0.67% yeast nitrogen base without amino acids, 20 μg/ml histidine) to a density of about $2 \times 10^7$ cells/ml, respectively. Then, cells were collected, suspended in Zymolyase solution [1.2M sorbitol, 50 mM potassium phosphate (pH 7.2), 14 mM 2-mercaptoethanol, 0.4 mg/ml Zymolyase 60,000] and incubated at 30° C. for 1 hour. To spheroplasts recovered by centrifugation was added a buffer solution [1% SDS, 50 mM Tris-HCl (pH 6.8), 10% 2-mercaptoethanol, 40% glycerol, 0.02% bromphenol blue, 1 mM phenylmethyl-sulfonyl fluoride] and the mixture was heated for 5 minutes at 100° C. to solubilize protein. After removal of insoluble matter, this was electrophoresed using 7.5% SDS-polyacrylamide gel. Migrated protein in polyacrylamide were electrophoretically blotted on a nitrocellulose filter in 25 mM Tris-HCl, 192 mM glycine, 20% methanol. The blotted filter was dipped in TBS buffer solution [50 mM Tris-HCl (pH 7.5), 200 mM NaCl] and then incubated at 37° for 40 minutes in TBS buffer solution containing 3% gelatin and 0.05% Tween 20 and then incubated at 37° C. for 2 hours in TBS buffer solution containing 50 μg of anti-P-450MC antibody or 30 μg of anti-reductase antibody, and 1% gelatin and 0.05% Tween 20. After reaction with antibody, the filter was washed 4 times with TBS buffer solution containing 0.05% Tween 20 at 37° C. for each 30 minutes and then incubated at 37° C. for 20 minutes in TBS buffer solution containing 3% gelatin and 0.05% Tween 20. Subsequently, the filter was incubated at 37° C. for 1 hour in TBS buffer solution containing 2 μCi of [$^{125}$I] protein A (Amersham), 1% gelatin and 0.05% Tween 20 and was washed 4 times at 37° C. for each 30 minutes with TBS buffer solution containing 0.05% Tween 20. The filter was air-dried and then subjected to autoradiography. It was recognized that strains AH22 (pAMP19), AH22 (pALP1), AH22 (pALP17), AH22 (pALP25) and AH22 (pALP4) all produced proteins which reacted with both anti-P-450MC and anti-reductase antibodies. The produced proteins had an apparent molecular weight of about 130,000–140,000 daltons on SDS-polyacrylamide gel electrophoresis. This value was nearly the same as the molecular weight calculated from the constructed chimeric fused enzyme gene of P-450 and reductase.

The transformed yeast strains AH22 (pAMP19), AH22 (pALP1), AH22 (pALP17), AH22 (pALP25) and AH22 (pALP4) cultivated to a density of about $2 \times 10^7$ cells/ml in SD-synthetic medium were collected, washed with 100 mM potassium phosphate (pH 7.0) and then resuspended in 2 ml of 100 mM potassium phosphate (pH 7.0). 1 ml each of the cell suspension was poured into two cuvettes, respectively and carbon monoxide was bubbled into the cuvette of sample side. Then, 5–10 mg of dithionite was added to both the cuvettes. After well stirring, difference spectrum of 400-500 nm was measured and heme-containing P-450 content was calculated based on the value $\Delta\epsilon=91$ $mM^{-1}cm^{-1}$ from the difference in absorbance at 447 nm and 490 nm. As shown in Table 1, it was found that strains AH22 (pAMP19), AH22 (pALP1), AH22 (pALP17), AH22 (pALP25) and AH22 (pALP4) produced about $6-7 \times 10^4$ molecules of heme-containing P-450/reductase chimeric fused proteins per cell, respectively.

EXAMPLE 5

Measurement of Acetaminophene Produced from Acetanilide by the Transformed Yeast Strain The transformed yeast strains AH22 (pAMC1), AH22 (pAMP19), AH22 (pALP1), AH22 (pALP17), AH22 (pALP25) and AH22 (pALP4) were cultivated to a density of about $2 \times 10^7$ cells/ml in SD-synthetic medium and to each culture medium was added 1.5M acetanilide (methanolic solution) to a final concentration of 25 mM. Thereafter, under continuous cultivation, a given amount of the culture medium was taken every one hour and centrifuged to remove cells. Supernatant of the culture medium was subjected HPLC (high performance liquid chromatography) to measure amount of acetaminophene produced.

HPLC was effected by employing $\mu$ Bondapak C18 (4×300 mm), elution with methanol:water:acetic acid (15:84:1 V/V %) and monitoring the absorbance at 245 nm. As shown in Table 1, acetaminophene production by P-450 reductase chimeric fused enzyme producing strain AH22 (pAMP19) was about 60% of that by P-450MC producing strain AH22 (pAMC1). From the fact that cellular amount of heme-containing enzyme in AH22 (pAMP19) was about 1/6 of that in strain AH22 (pAMC1), it was suggested that the acetaminophene-producing activity per enzyme protein increased to about four times. Furthermore, the activities of strains AH22 (pALP1), AH22 (pALP17), AH22 (pALP25) and AH22 (pALP4) for production of acetaminophene were nearly the same as that of AH22 (pAMP19). Since the amount of heme-containing enzyme in these strains were lower than that in AH22 (pAMC1), like strain AH22 (pAMP19), the activity per enzyme protein of these strains was 3-4 times higher than that of P-450MC singly producing strain.

From the above results, it has become clear that the chimeric fused enzyme of P-450MC and reductase constitutes electron-transport chains more efficiently than in case of P-450MC single expression to show higher monooxygenase activity.

EXAMPLE 6

Purification of Chimeric Fused Monooxygenase Comprising P-450 and Reductase

The chimeric fused monooxygenase comprising P-450MC and reductase was isolated from strain AH22 (pAMP19) which produced the monooxygenase. Strain AH22 (pAMP19) of about $3 \times 10^{11}$ cells was suspended in Zymolyase solution and incubated at 30° C. for 1 hour. Thereafter, the spheroplasts were collected by centrifugation. The spheroplasts were washed twice with 50 mM potassium phosphate (pH 7.2), 14 mM 2-mercaptoethanol, 1.2M sorbitol and then subjected to ultrasonic treatment (60 w, 5 minutes) to disrupt the cells. Supernatant obtained by sequential centrifugations of 3,000×g for 10 minutes and 10,000×g for 20 minutes was further centrifuged at 125,000×g for 90 minutes to precipitate the microsomal fraction. To the microsomal fraction containing 20 nmol of P-450/reductase chimeric fused enzyme were added 60 ml of buffer solution A [10 mM potassium phosphate (pH 7.4), 0.1 mM EDTA, 20% glycerol, 0.5% sodium cholate, 0.2% Emulgen 913] and phenylmethyl-sulfonyl fluoride in an amount of 1 mM in final concentration and the mixture was stirred at 4° C. for 10 minutes. Then, this was applied to a DEAE-cellulose column (1.6×12 cm) equilibrated with buffer solution A and washed with 20 ml of buffer solution A. The orange band at the central part of the column was recovered and applied to a new DEAE-cellulose column (1.6×12 cm) and eluted with buffer solution A with 0-40 mM KCl linear gradient. By monitoring the absorbance at 417 nm, two peaks were recognized. The reduced CO-difference spectrum (cf. Examples 4) of the two peak fractions indicated that the P-450/reductase chimeric fused monooxygenase was included in the peak which was eluted faster. Thus, this fraction was recovered and applied to 2',5'-ADP-Sepharose 4B column (0.9×3 cm) previously equilibrated with buffer solution A and washed with 40 ml of buffer solution A. Then, elution with buffer solution A containing 0.5 mM NADP+ resulted in a fraction which contained the purified P-450/reductase chimeric fused monooxygenase sample.

Specific content of P-450/reductase chimeric fused monooxygenase in the microsomal fraction was 0.09 nmol/mg pretein, but was increased to 1.14 nmol/mg pretein by application to DEAE-cellulose column. Absorption spectrum of the fraction eluted from 2',5'-ADP Sepharose 4B column at 350-700 nm corresponded to spectrum of a sample which was a mixture (1:1) of P-450MC and rat reductase. This indicated that P-450/reductase chimeric fused monooxygenase contained in the molecule one molecule each of protoheme, flavin adenine mononucleotide and flavin mononucleotide. Furthermore, electrophoresis of purified sample on SDS-polyacrylamide gel showed nearly single band at the position of a molecular weight of about 130,000 daltons. To 100 $\mu$l of this purified sample (corresponding to 0.015 nmol P-450/reductase chimeric fused monooxygenase) were added 1.0 ml of 100 mM potassium phosphate (pH 7.4) and 25 $\mu$l of 20 mM NADPH and preincubation was effected at 37° C. for 3 minutes, followed by adding 500 nmol of 7-ethoxycoumarin and incubation for 5 minutes. The reaction was stopped by addition of 62.5 $\mu$l of 15% trichloroacetic acid and the reaction product, 7-hydroxycoumarin was measured. The O-deethylation activity of 7-ethoxycoumarin was 1.2 nmol/min/nmol P-450 which was similar to the activity in a reconstitutive system containing 0.015 nmol of rat P-450MC and 0.015 nmol of rat reductase. Thus, it has become clear that in the P-450/reductase chimeric fused monooxygenase sample, electrons from NADPH were transferred to P-450 within the molecule or between molecules and this single enzyme exhibits functions of both the P-450 and reductase enzymes. This enzyme cannot be produced by the conventional techniques and is utterly novel polyfunctional enzyme produced by protein engineering technique.

TABLE 1

Content of heme-containing P-450 protein in various transformed yeast strains and amount of acetaminophene produced by p-hydroxylation with acetanilide

| Strains | Heme-containing P-450 protein (molecule/cell) | Amount of acetaminophene produced (nmol/ml) |
|---|---|---|
| AH22 (pAMC1) | $4 \times 10^5$ | 4.7 |
| AH22 (pAMP19) | $7 \times 10^4$ | 2.9 |
| AH22 (pALP1) | $7 \times 10^4$ | 2.6 |
| AH22 (pALP17) | $7 \times 10^4$ | 3.3 |
| AH22 (pALP25) | $7 \times 10^4$ | 1.9 |
| AH22 (pALP4) | $6 \times 10^4$ | 2.9 |

We claim:

1. A genetically engineered microsomal monooxygenase having monooxygenase activity derived from cytochrome P-450 and reductase activity derived from NADPH-cytochrome P-450 reductase, which is constructed by linking the soluble region of the NADPH-cytochrome P-450 reductase to the C-terminal of the cytochrome P-450 in a single protein.

2. A monooxygenase according to claim 1, wherein the cytochrome P-450 is rat liver cytochrome P-450MC and the reductase is rat liver NADPH-cytochrome P-450 reductase.

3. A monooxygenase according to claim 2, wherein the cytochrome P-450MC and the reductase are bound by a linker of about 2 to 20 amino acids.

4. A monooxygenase according to claim 3, wherein the cytochrome P-450MC is defined by the amino acid residues 2-519 in FIG. 2 and the reductase is defined by amino acid residues 1-623 in FIG. 7.

5. A monooxygenase according to claim 4, wherein the amino acid sequence thereof is defined as shown in FIG. 2.

6. A monooxygenase according to claim 4, wherein the amino acid sequence thereof is defined as shown in FIG. 3.

7. A monooxygenase according to claim 4, wherein the amino acid sequence thereof is defined as shown in FIG. 4.

8. A monooxygenase according to claim 4, wherein the amino acid sequence thereof is defined as shown in FIG. 5.

9. A monooxygenase according to claim 4, wherein the amino acid sequence thereof is defined as shown in FIG. 6.

* * * * *